(12) United States Patent
Bednář et al.

(10) Patent No.: US 7,531,551 B2
(45) Date of Patent: May 12, 2009

(54) POLYMORPHS OF CABERGOLINE

(75) Inventors: Roman Bednář, Raduň (CZ); Ladislav Cvak, Zlatniky (CZ); Alexandr Jegorov, Dobra Voda (CZ); Roman Sobotik, Opava (CZ)

(73) Assignee: IVAX Pharmaceuticals s.r.o. (CZ)

( * ) Notice: Subject to any disclaimer, the term of this patent is extended or adjusted under 35 U.S.C. 154(b) by 464 days.

(21) Appl. No.: 10/841,813

(22) Filed: May 7, 2004

(65) Prior Publication Data

US 2005/0085499 A1    Apr. 21, 2005

Related U.S. Application Data

(60) Provisional application No. 60/539,494, filed on Jan. 27, 2004, provisional application No. 60/468,887, filed on May 8, 2003.

(51) Int. Cl.
*A61K 31/48*    (2006.01)
*C07D 457/06*    (2006.01)

(52) U.S. Cl. .................. 514/288; 546/69; 546/67

(58) Field of Classification Search ........... 514/288; 546/69, 67
See application file for complete search history.

(56) References Cited

U.S. PATENT DOCUMENTS

| | | | |
|---|---|---|---|
| 4,526,892 A | 7/1985 | Salvati et al. | |
| 6,727,363 B2 | 4/2004 | Tomasi et al. | |
| 7,026,483 B2 * | 4/2006 | Gutman et al. | 546/69 |
| 7,186,837 B2 | 3/2007 | Greenwood et al. | |
| 2002/0123503 A1 | 9/2002 | Ross et al. | |
| 2002/0177709 A1 | 11/2002 | Gutman et al. | |
| 2003/0045539 A1 | 3/2003 | Gomez-Mancilla | |
| 2003/0144516 A1 | 7/2003 | Candiani et al. | |
| 2003/0149067 A1 | 8/2003 | Tomasi et al. | |
| 2003/0187013 A1 | 10/2003 | Tomasi et al. | |
| 2004/0072855 A1 | 4/2004 | Tomasi et al. | |
| 2004/0092744 A1 | 5/2004 | Tomasi et al. | |
| 2004/0209910 A1 | 10/2004 | Gutman et al. | |
| 2005/0245560 A1 | 11/2005 | Greenwood et al. | |
| 2006/0281777 A1 | 12/2006 | Ahmad et al. | |

FOREIGN PATENT DOCUMENTS

| | | | |
|---|---|---|---|
| CZ | 287176 | | 10/1997 |
| WO | WO-01/70740 | | 9/2001 |
| WO | WO-01/72746 | | 10/2001 |
| WO | WO-01/72747 | | 10/2001 |
| WO | WO-03/078392 | | 9/2003 |
| WO | WO 03/078433 | * | 9/2003 |
| WO | 2005085243 | | 9/2005 |
| WO | 2007/091039 | | 8/2007 |

OTHER PUBLICATIONS

ILFARMACO;50;175-178 (1995).
Supplementary European Search Report, EP 04751664.

* cited by examiner

*Primary Examiner*—Charanjit S Aulakh
(74) *Attorney, Agent, or Firm*—Lerner, David, Littenberg, Krumholz & Mentlik, LLP

(57) ABSTRACT

Provided are new crystalline Forms VIII, IX, XI, XII, XIV, XV, XVI, XVII, and XVIII of cabergoline. Also provided are novel processes for preparation of cabergoline Form I, Form II, Form VII, and amorphous cabergoline.

71 Claims, 12 Drawing Sheets

POLYMORPHS OF CABERGOLINE

CROSS-REFERENCE TO RELATED APPLICATIONS

This application claims the benefit of Provisional Applications Ser. Nos. 60/468,887, Application date May 8, 2003 and 60/539,494, Application date Jan. 27, 2004, all of which are incorporated herein by reference.

FIELD OF THE INVENTION

The present invention relates to the solid state chemistry of cabergoline.

BACKGROUND OF THE INVENTION

Cabergoline is a generic name of 1-((6-allylergolin-8β-yl)-carbonyl)-1-(3-dimethylaminopropyl)-3-ethylurea. The compound and the process for its preparation were disclosed in the U.S. Pat. No. 4,526,892, which is herein incorporated by reference. Another process for manufacture of cabergoline was described in Czech Pat. 287 176. Cabergoline is a selective and long lasting dopamine D2 agonist and it is used for treatment of hyperprolactinemia, parkinsonism, and other related diseases.

Cabergoline was described in several crystalline forms. The first crystalline form of cabergoline was described in Il Farmaco, 50, 175-178 (1995), which was latter designated as cabergoline Form I. This form was prepared by crystallisation from diethylether. A new process for preparing the crystalline Form I of cabergoline was described recently in two patent applications WO 01/70740 and WO 03/078392. According to the first one the Form I can be prepared via a new toluene solvate denominated as Form V. The toluene solvate Form V affords the Form I by drying at the temperature from 40 to 65° C., using high vacuum. According to WO 03/078392 the Form I can be prepared via a new toluene hemi-solvate Form X. The solvate X is described in WO 03/078392 as a true solvate having a fixed composition of about 0.5 toluene moles per mole of cabergoline. Form X is unstable and it can be very easily transferred to the Form I even when dried in vacuum at ambient temperature.

Two new anhydrous and unsolvated forms of cabergoline were described recently. Form II, obtained by crystallisation from diethylether and other solvents with similar polarity was described in WO 01/72747. Form VII was obtained by solvent (diethylether, hexane, heptane) mediated phase transition of the Form I at relatively high temperature (from 30 to 80° C.) as described in WO 01/72746. The physical properties of both new forms are very similar to that of the Form I and therefore it does not seem that the new forms can bring any advantage to the use of cabergoline in formulation of drugs.

Crystallisation of cabergoline is difficult, e.g., the crystallisation of the Form II was accomplished by several days cooling and mixing of the solution of purified cabergoline in diethylether. Also the Form I can be obtained by crystallisation from diethylether but its polymorph purity is poor due to the presence of the Form II. Also the yields of the crystalline products obtained by the crystallisation from diethylether are not satisfactory. Therefore, a process producing reproducibly the Form I or any other form and affording high yield of the product is still advisable.

The various crystalline forms have different properties as the result of different arrangement of molecules in the crystal structure, different density of packing, and/or different hydrogen-bond network. Accordingly, individual crystalline forms may be thought of as distinct solids having distinct advantageous and/or disadvantageous physical properties compared to other forms.

All the above mentioned forms are characterised by their IR, DSC, solid state NMR and distinct X-ray powder diffraction patterns defined as a list of 2θ values obtained with certain source of X-ray radiation, which can be easily calculated for any other source of radiation by the Bragge equation. The complete crystal structure determined by X-ray structural analysis was described only for the Form I (Il Farmaco, 50, 175-178 (1995)).

SUMMARY OF THE INVENTION

In one aspect the present invention provides a roughly isostructural series of orthorhombic cabergoline solvates characterised by data selected from the group consisting of a powder X-ray diffraction pattern with peaks at about 9.3, 12.3, 13.8, 16.0, 19.4, 20.0, 20.4, 21.3, 24.8, 25.1, and 28.1±0.2 degrees two-theta using CoKα radiation at ambient temperature, symmetry P $2_1 2_1 2_1$, unit cell parameters about a=12.9, b=14.3, c=17.7 Å determined at 150 K, and chemical composition cabergoline:solvent approximately 1:1. Said solid crystalline forms denote cabergoline Form VIII for cabergoline tert-butyl methyl ether solvate, Form XIV for cabergoline tetrahydropyrane solvate, and Form XV for cabergoline cyclohexane solvate, respectively. In another aspect, the present invention provides a process for preparing crystalline cabergoline solvate having at least one of the characteristic of roughly isostructural series of orthorhombic cabergoline solvates (such as the X-ray powder pattern, unit cell parameters, and/or chemical composition) comprising the steps of preparing a solution of cabergoline in tert-butyl methyl ether, tetrahydropyrane or cyclohexane, or in a solvent mixture containing them, cooling the solution, removing a part of solvent by distillation, and/or admixing an antisolvent in which is cabergoline insoluble in order to precipitate cabergoline Forms VIII, XIV or XV, respectively, and separating cabergoline Forms VIII, XIV or XV.

In another aspect the present invention provides crystalline cabergoline solvate characterised by data selected from the group consisting of a powder X-ray diffraction pattern with peaks at about 9.5, 11.0, 11.1, 12.3, 15.7, 18.5, 19.4, 20.1, 20.6, 20.9, 24.8, 25.0, 26.4, 27.5, and 30.3±0.2 degrees two-theta using CoKα radiation, symmetry P $2_1 2_1 2_1$, unit cell parameters a=13.0, b=13.4, c=18.5 Å at 293 K, and chemical composition cabergoline: toluene approximately 1:1. Said solid crystalline form denotes cabergoline Form IX.

In another aspect, the present invention provides a process for preparing crystalline cabergoline solvate having at least one of the characteristic of Form IX (such as the X-ray powder pattern, unit cell parameters, and/or chemical composition) comprising the steps of preparing a solution of cabergoline in toluene or a solvent mixture containing it, cooling the solution to about −10° C. in order to precipitate cabergoline Form IX and separating cabergoline Form IX.

In another aspect the present invention provides crystalline cabergoline solvate characterised by data selected from the group consisting of a powder X-ray diffraction pattern with peaks at about 8.9, 12.3, 16.8, 17.3, 18.9, 19.3, 19.9, 20.4, 24.1, 24.3, 25.0, 25.9, 26.7, 27.3, 27.7, and 30.9±0.2 degrees two-theta using CoKα radiation at ambient temperature, endothermic peak at about 63° C., and chemical composition cabergoline:p-xylene approximately 1:1. Said solid crystalline form denotes cabergoline Form XI.

In another aspect, the present invention provides a process for preparing crystalline cabergoline solvate having at least one of the characteristic of Form XI (such as the X-ray powder pattern, DSC, and/or chemical composition) comprising the steps of preparing a solution of cabergoline in a solvent mixture containing p-xylene, cooling the solution below −10°

C., adding seeds of cabergoline Form I or XI in order to precipitate cabergoline Form XI and separating cabergoline Form XI.

In another aspect the present invention provides crystalline cabergoline solvate characterised by data selected from the group consisting of a powder X-ray diffraction pattern with peaks at 9.4, 10.9, 12.2, 13.4, 15.3, 15.5, 16.6, 17.1, 18.3, 19.2, 20.5, 24.1, 24.8, 26.8, 27.2, 27.6, 28.2, 28.5, 30.0, and 32.1±0.2 degrees two-theta using CoKα radiation determined at ambient temperature, and chemical composition cabergoline:o-xylene approximately 1:1. Said solid crystalline form denotes cabergoline Form XII.

In another aspect, the present invention provides a process for preparing crystalline cabergoline solvate having at least one of the characteristic of Form XII (such as the X-ray powder pattern, and/or chemical composition) comprising the steps of preparing a solution of cabergoline in o-xylene or a solvent mixture containing it, cooling the solution to about −10° C. in order to precipitate cabergoline Form XII and separating cabergoline Form XII.

In another aspect the present invention provides crystalline cabergoline solvate characterised by data selected from the group consisting of a powder X-ray diffraction pattern with peaks at about 9.5, 11.2, 12.4, 13.3, 15.4, 16.8, 17.7, 18.6, 19.2, 20.7, 24.0, 25.7, 26.1, 26.7, 27.4, 28.8, 30.0, and 33.1±0.2 degrees two-theta using CoKα radiation at ambient temperature, symmetry $P2_12_12_1$, unit cell parameters a=12.8, b=12.9, c=19.2 Å determined at 150 K, and chemical composition cabergoline:p-xylene approximately 1:1. Said solid crystalline form denotes cabergoline Form XVI.

In another aspect, the present invention provides a process for preparing crystalline cabergoline solvate having at least one of the characteristic of Form XVI (such as the X-ray powder pattern, unit cell parameters, and/or chemical composition) comprising the steps of preparing a solution of cabergoline in a solvent mixture containing p-xylene, cooling the solution to about −10° C. in order to precipitate cabergoline Form XVI and separating cabergoline Form XVI.

In another aspect the present invention provides crystalline cabergoline solvate characterised by data selected from the group consisting of a powder X-ray diffraction pattern with peaks at about 9.4, 12.2, 15.3, 16.6, 17.4, 17.8, 18.3, 19.0, 20.5, 23.8, 24.2, 26.7, 27.1, and 27.5±0.2 degrees two-theta using CoKα radiation determined at ambient temperature, symmetry $P2_12_12_1$, unit cell parameters a=12.9, b=13.1, c=19.1 Å determined at 150 K, and chemical composition cabergoline: 1,2,4-trimethylbenzene approximately 1:1. Said solid crystalline form denotes cabergoline Form XVII.

In another aspect, the present invention provides a process for preparing crystalline cabergoline solvate having at least one of the characteristic of Form XVII (such as the X-ray powder pattern, unit cell parameters, and/or chemical composition) comprising the steps of preparing a solution of cabergoline in 1,2,4-trimethylbenzene or a solvent mixture containing it, cooling the solution to about −10° C. in order to precipitate cabergoline Form XVII and separating cabergoline Form XVII.

In another aspect the present invention provides crystalline cabergoline solvate characterised by data selected from the group consisting of a powder X-ray diffraction pattern with peaks at 8.7, 9.1, 12.3, 13.3, 17.0, 17.4, 19.1, 19.2, 19.7, 20.0, 21.8, 22.5, 24.1, 27.0, 27.3, 28.5, and 30.8±0.2 degrees two-theta using CoKα radiation determined at ambient temperature, and chemical composition cabergoline:ethylbenzene approximately 1:1. Said solid crystalline form denotes cabergoline Form XVIII.

In another aspect, the present invention provides a process for preparing crystalline cabergoline solvate having at least one of the characteristic of Form XVIII (such as the X-ray powder pattern, and/or chemical composition) comprising the steps of preparing a solution of cabergoline in ethylbenzene or a solvent mixture containing it, cooling the solution below −10° C., adding seeds of cabergoline Form I in order to precipitate cabergoline Form XVIII and separating cabergoline Form XVIII.

In another aspect present invention provides new process for obtaining cabergoline Form I. Cabergoline Form I can be prepared by desolvation of new cabergoline solvates. Preferably desolvation is carried out by using vacuum. Preferably, cabergoline Form I is obtained by desolvation of cabergoline Form XI.

In another aspect present invention provides new process for obtaining cabergoline Form I. Cabergoline Form I can be prepared by direct crystallisation comprising the steps of preparing a solution of cabergoline in toluene or a solvent mixture containing it, cooling the solution below −10° C., adding seeds of cabergoline Form I in order to precipitate cabergoline Form I and separating cabergoline Form I.

In another aspect present invention provides new process for obtaining cabergoline Form II. Cabergoline Form II can be prepared by desolvation of new cabergoline solvates. Preferably desolvation is carried out by using vacuum. Preferably, cabergoline Form II is obtained by desolvation of cabergoline Form XII.

In another aspect present invention provides a new process for purification of cabergoline by crystallisation in a form of cabergoline solvates. Preferably, cabergoline Form VIII is used for purification of crude cabergoline prepared by the chemical synthesis.

In another aspect present invention provides new process for obtaining unsolvated cabergoline Forms I, II, and/or VII. Said unsolvated cabergoline forms can be prepared by phase transition of the new cabergoline solvates in suspension created by a solvent providing unsolvated cabergoline forms preferably under the temperature control. Preferably, phase transition is carried out in suspension in aliphatic hydrocarbons or their mixtures.

In another aspect present invention provides new process for obtaining amorphous cabergoline. The amorphous cabergoline is prepared by dissolving any crystalline form of cabergoline in a solvent in which cabergoline is soluble and after evaporation of the solvent, solid amorphous foam of cabergoline is obtained. The solvents suitable for this use are volatile ethers, ketones and esters. Preferred solvent is acetone or its mixture with diethylether. Alternatively, amorphous cabergoline is prepared by dissolving cabergoline in a solvent with the melting point in the range from −80 to +30° C. and freeze drying of the solution obtained. The preferred solvent for this use is tert-butyl alcohol or 1,4-dioxane.

A still further embodiment of the present invention is a method of treating of central nervous system disorders or hyperprolactinemia with a pharmaceutical composition containing a therapeutically effective amount of a new cabergoline solvate and/or amorphous solid state form of cabergoline. Provided that the daily dose of cabergoline is very low, present invention describes also new approach of crystal engineering consisting in the design of stable cabergoline solvates with physiologically acceptable solvent.

BRIEF DESCRIPTION OF THE DRAWINGS

The invention is further described by the following non-limiting examples, which refer to the accompanying FIGS. 1 to 12, which are briefly described below.

DETAILED DESCRIPTION OF THE DRAWINGS

The present invention provides new crystalline forms of cabergoline and new processes for their preparation as well as new processes for preparation of Forms I and II and amorphous cabergoline.

It was found out that cabergoline crystallises from several solvents as a crystalline solvate. Unexpectedly, the crystallisation is so easy, that the crystalline solvate can be prepared even when a crude reaction mixture obtained by the chemical synthesis is subjected to crystallisation.

Figure 1:
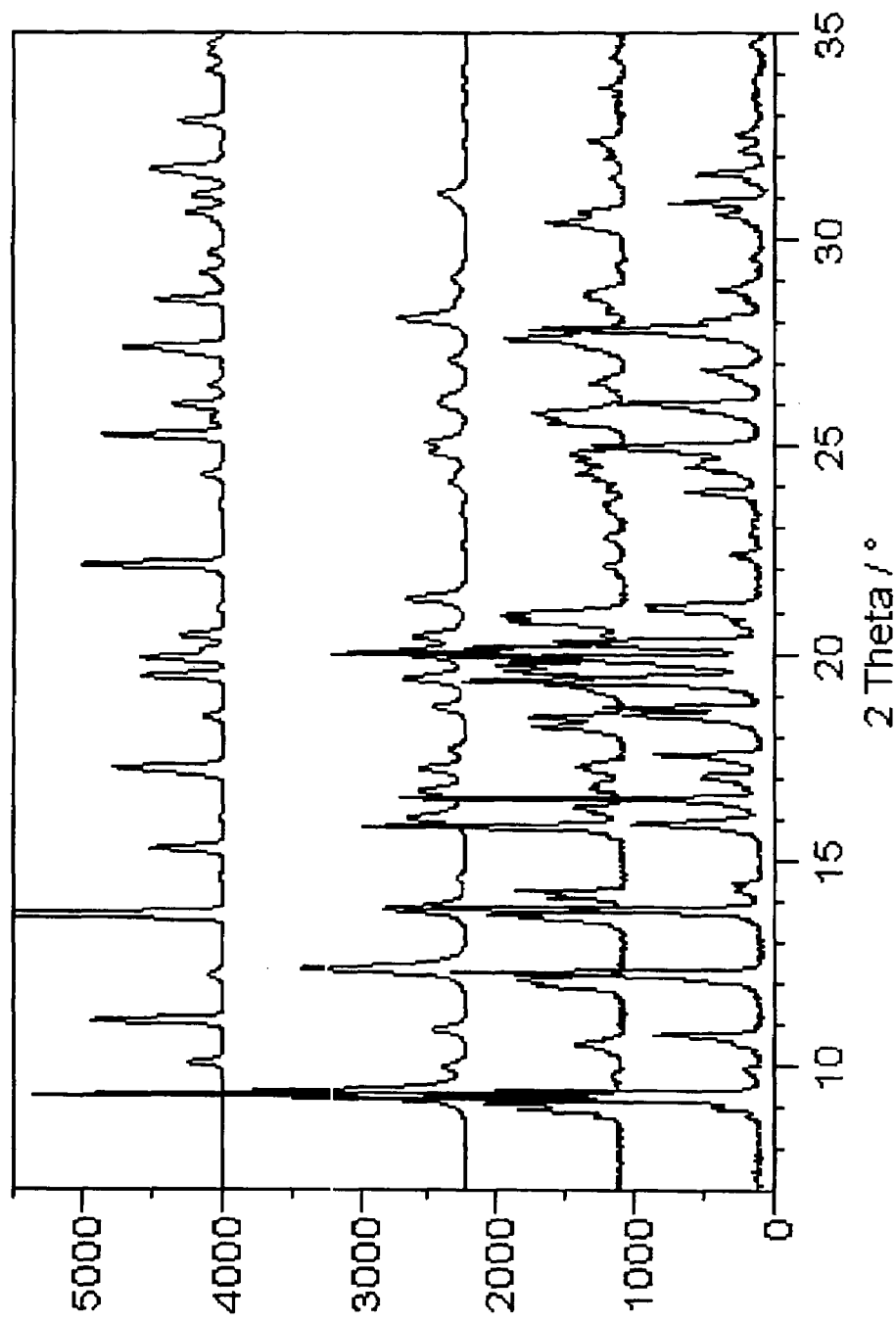
FIG. 1 represents a comparison of characteristic powder diffraction patterns of known cabergoline Form II and examples of orthorhombic forms of cabergoline solvates obtained using CoKα radiation. From the top the first curve is calculated powder pattern of cabergoline Form II, the second one is calculated powder pattern of cabergoline tert-butyl methyl ether solvate Form VIII (150 K), the third one is experimental powder pattern of cabergoline cyclohexane solvate Form XV, and the fourth one at the bottom is experimental powder pattern of cabergoline tetrahydropyrane solvate Form XIV.

In a first aspect, the present invention provides a new crystalline form of cabergoline, designated Form VIII. Cabergoline Form VIII is characterised by a powder X-ray diffraction pattern (FIG. 1) with peaks at about as described in Table 1 (±0.2 degrees two-theta) using a XRD 3000P diffractometer Seifert with CoKα radiation, λ=1.79027 Å, at laboratory temperature, and chemical composition cabergoline:tert-butyl methyl ether approximately 1:1. Thus the cabergoline Form VIII differs from all previously described forms of cabergoline by the summary composition $C_{31}H_{49}N_5O_3$ and molecular weight 539.8.

Cabergoline Form VIII exhibits the following cell parameters symmetry P $2_12_12_1$, a=12.942(3), b=14.304(3), c=17.690(3) Å, V=3274.8 Å$^3$ as determined by crystal structure determination on Enraf-Nonius CAD 4 diffractometer, λ (CuKα)=1.54184 Å, at 293 K. We provide evidence here that the cell parameters of various cabergoline forms can be affected by the temperature used for the crystal structure determination or measurement of their powder diffraction data. Thus cabergoline Form VIII exhibits the following cell parameters symmetry P $2_12_12_1$, a=12.730, b=14.138, c=17.548 Å, V=3158.1 Å$^3$ as determined by crystal structure determination on Nonius Kappa CCD area detector, λ(MoKα)=0.71073 Å at 150 K.

Table I: X-ray powder diffraction data of cabergoline Form VIII using CoKα radiation.

TABLE I

|  | angle | D | I rel |
|---|---|---|---|
| 1. | 9.327 | 11.0017 | 1000.0 |
| 2. | 12.342 | 8.3214 | 676.8 |
| 3. | 13.793 | 7.4497 | 338.5 |
| 4. | 16.000 | 6.4275 | 243.5 |
| 5. | 19.393 | 5.3108 | 257.9 |
| 6. | 20.010 | 5.1488 | 343.2 |
| 7. | 20.406 | 5.0497 | 219.9 |
| 8. | 21.311 | 4.8377 | 255.3 |
| 9. | 24.842 | 4.1587 | 141.9 |
| 10. | 25.087 | 4.1187 | 164.2 |
| 11. | 28.097 | 3.6850 | 281.3 |

The present invention further provides a process for preparing cabergoline Form VIII comprising the steps of preparing a solution of cabergoline in tert-butyl methyl ether or a solvent mixture containing it, cooling the solution, removing a part of solvent by distillation, and/or admixing an antisolvent in which cabergoline is insoluble in order to precipitate cabergoline Form VIII and separating cabergoline Form VIII.

In another aspect, the present invention provides a new crystalline form of cabergoline, designated Form XIV. Cabergoline Form XIV is characterised by a powder X-ray diffraction pattern (FIG. 1) using a XRD 3000P diffractometer Seifert with CoKα radiation, λ=1.79027 Å, at laboratory temperature, and chemical composition cabergoline:tetrahydropyrane approximately 1:1. Thus the cabergoline Form XIV differs from all previously described forms of cabergoline by the summary composition $C_{31}H_{47}N_5O_3$ and molecular weight 537.7.

The present invention further provides a process for preparing cabergoline Form XIV comprising the steps of preparing a solution of cabergoline in tetrahydropyran or a solvent mixture containing it, cooling the solution, removing a part of solvent by distillation, and/or admixing an antisolvent in which cabergoline is insoluble in order to precipitate cabergoline Form XIV and separating cabergoline Form XIV.

In another aspect, the present invention provides a new crystalline form of cabergoline, designated Form XV. Cabergoline Form XV is characterised by a powder X-ray diffraction pattern (FIG. 1) using a XRD 3000P diffractometer Seifert with CoKα radiation, λ=1.79027 Å, at laboratory temperature, and chemical composition cabergoline:cyclohexane approximately 1:1. Thus the cabergoline Form XV differs from all previously described forms of cabergoline by the summary composition $C_{32}H_{49}N_5O_3$ and molecular weight 535.8.

Cabergoline Form XV exhibits the following cell parameters symmetry P $2_12_12_1$, a=12.912(2), b=14.355(2), c=17.367(3) Å, V=3219.1(9) Å$^3$ as determined by crystal structure determination on Enraf-Nonius CAD 4 diffractometer, λ (CuKα)=1.54184 Å, at 293 K.

In another aspect, the present invention provides a process for preparing cabergoline Form XV comprising the steps of preparing a solution of cabergoline in a solvent in which cabergoline is soluble, adding cyclohexane, removing a part of solvent by distillation, and/or cooling the solution in order to precipitate cabergoline Form XV and separating cabergoline Form XV.

Although cabergoline Forms VIII, XIV, and XV are structurally related (FIG. 1), they represent distinct forms, which differ in their summary composition, lattice parameters, and by ICH classification of incorporated solvents. We disclose here that the choice of a solvent to be incorporated is based on the principle of crystal engineering, which uses the free solvent accessible area calculated from the crystal structure determination of this orthorhombic form. Thus for example, in the structure of cabergoline cyclohexane solvate with lattice parameters a=12.9 Å, b=14.4 Å, and c=17.4 Å, Z=4, determined at ambient temperature by crystal structure determination, there are four solvent areas each with the volume about 230 Å$^3$, which can be occupied by a solvent molecule. Similarly, the solvent area 240 Å$^3$, available for one solvent molecule in cabergoline tert-butyl methyl ether solvate was determined. Based on the free solvent accessible area calculated from these structures another suitable solvents can be designed, which can be also incorporated into the structure, e.g., tetrahydropyrane.

The crystallisation can be accomplished when a solution of cabergoline in a suitable solvent, e.g., tert-butyl methyl ether, is partially evaporated or the concentrated solution is cooled. Another way how to prepare cabergoline solvate is the addition of a suitable solvent, e.g. cyclohexane, to a concentrated solution of cabergoline in a solvent in which cabergoline is well soluble. Such solvent can be from a group of aliphatic ethers, ketones and esters, like diethylether, acetone and ethyl acetate, or their mixture. The solution can be again brought to crystallisation, e.g., by cooling. The solution of cabergoline can be brought to crystallisation also by addition of a solvent in which the particular cabergoline solvate is insoluble, like aliphatic hydrocarbons e.g. hexane or heptane. Similarly, if cyclohexane is added to the solution of cabergoline in a solvent with the lower boiling point than cyclohexane, the partial evaporation of the solution provides crystalline cabergoline cyclohexane solvate. Also any combination of the above mentioned techniques or a mixture of solvents can be used to bring the solution to crystallisation of desired cabergoline solvate.

The crystallisation of cabergoline from tert-butyl methyl ether or another solvent is an excellent process for purification of cabergoline prepared by chemical synthesis. Such purification is demonstrated in the Example 1. The material with the purity 83.4% was subjected to crystallisation from tert-butyl methyl ether and a crystalline product with purity 99.2% was obtained in excellent yield.

Figure 2:
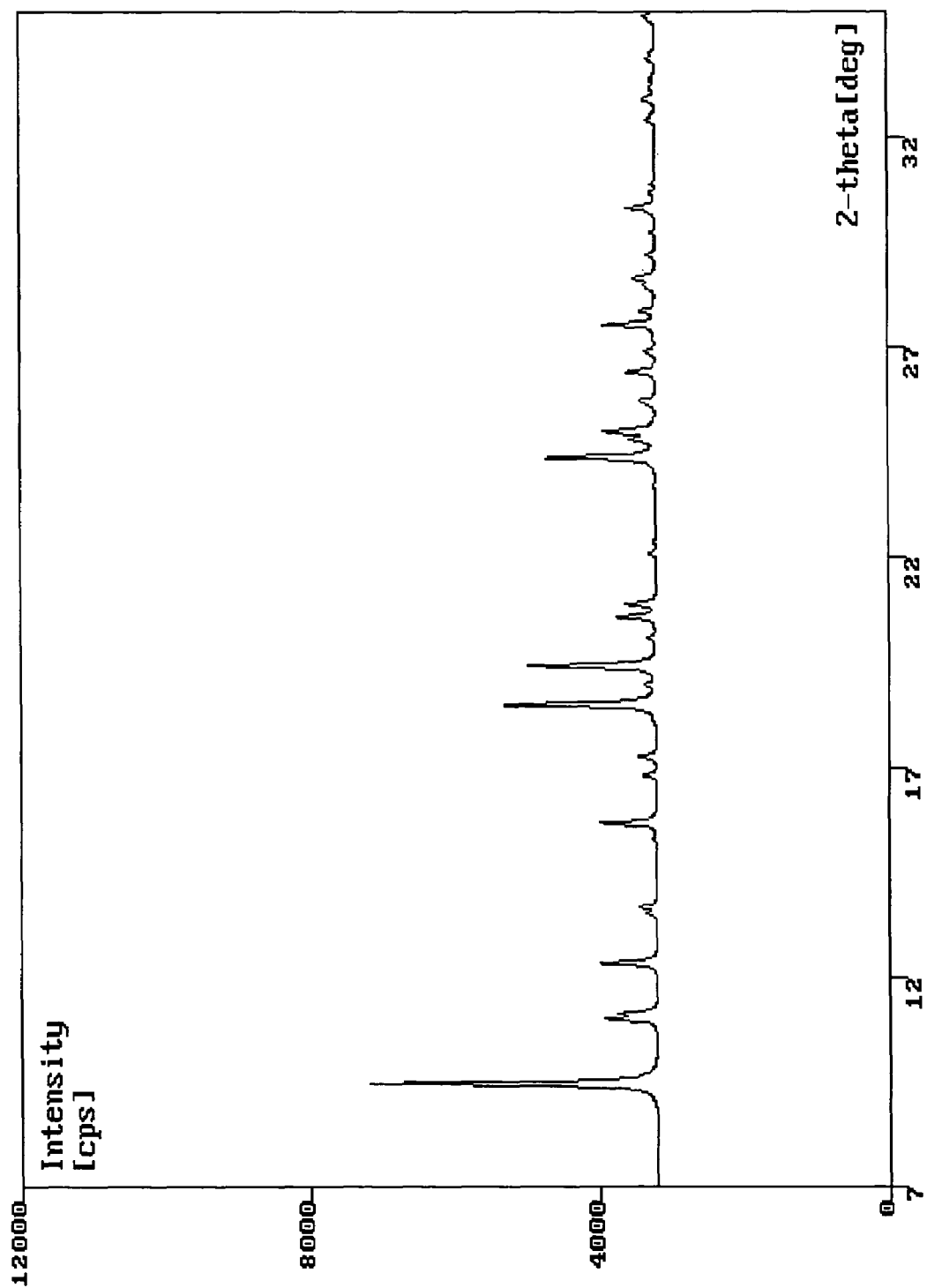
FIG. 2 represents powder diffraction pattern of cabergoline toluene solvate Form IX using CoKα radiation.

In another aspect, the present invention provides a new crystalline form of cabergoline, designated Form IX. Cabergoline Form IX is characterised by a powder X-ray diffraction pattern (FIG. 2) with peaks at about as described in Table 2 (±0.2 degrees two-theta) using a XRD 3000P diffractometer Seifert with CoKα radiation, λ=1.79027 Å, at laboratory temperature, and chemical composition cabergoline:toluene approximately 1:1. Cabergoline Form IX exhibits summary composition $C_{33}H_{45}N_5O_2$, molecular weight 543.7, and differs from all previously described forms of cabergoline by its powder pattern.

Table II: X-ray powder diffraction data of cabergoline Form IX using CoKα radiation.

TABLE II

|  | angle | D | I rel |
|---|---|---|---|
| 1. | 9.450 | 10.8597 | 1000.0 |
| 2. | 11.002 | 9.3307 | 185.2 |
| 3. | 11.127 | 9.2266 | 136.1 |
| 4. | 12.334 | 8.3268 | 200.4 |
| 5. | 15.675 | 6.6597 | 196.7 |
| 6. | 18.491 | 5.5675 | 530.6 |
| 7. | 19.413 | 5.3056 | 447.8 |
| 8. | 20.066 | 5.1346 | 29.6 |
| 9. | 20.576 | 5.0086 | 137.1 |
| 10. | 20.886 | 4.9350 | 104.6 |

TABLE II-continued

|  | angle | D | I rel |
|---|---|---|---|
| 11. | 24.388 | 4.2349 | 376.2 |
| 12. | 25.000 | 4.1328 | 179.6 |
| 13. | 26.414 | 3.9152 | 102.0 |
| 14. | 27.535 | 3.7587 | 181.2 |
| 15. | 30.318 | 3.4207 | 103.1 |

Cabergoline Form IX exhibits the following cell parameters symmetry P $2_12_12_1$, a=12.982, b=13.444, c=18.459 Å, V=3221.5 Å$^3$ as determined by crystal structure determination on Enraf-Nonius CAD 4 diffractometer, λ (CuKα)= 1.54184 Å, at 293 K. We provide evidence here that, similarly as with other forms, the cell parameters of cabergoline Form IX can be affected by the temperature used for the crystal structure determination or measurement of their powder diffraction data. Thus cabergoline Form IX exhibits the following cell parameters symmetry P $2_12_12_1$, a=12.8290(1), b=13.3170(2), c=18.1210(2) Å, V=3095.86(6) Å$^3$ as determined by crystal structure determination on Nonius Kappa CCD area detector, λ(MoK$_α$)=0.71073 Å at 150 K.

In another aspect, the present invention provides a process for preparing cabergoline Form IX comprising the steps of preparing a solution of cabergoline in toluene or a solvent mixture containing it, cooling the solution to the temperature below 0° C., preferably to −10° C. in order to precipitate cabergoline Form IX and separating cabergoline Form IX. Cabergoline Form IX is preferably prepared by standing of cabergoline solution in refrigerator at about −10° C. without seeding with other forms providing thus cabergoline Form IX in large prismatic crystals.

In another aspect it was found out that cabergoline crystallises at low temperature from several alkyl-aromatic solvents as crystalline solvates. Cabergoline solvates with alkyl-aromatic solvents have the general formula $C_6H_5R^1$, where for $R^1$=ethyl, propyl or isopropyl or formula $C_6H_{6-x}R^1_iR^2_jR^3_kR^4_lR^5_mR^6_n$, where x=2, 3, 4, 5, 6, sum of i+j+k+l+m+n=x, and $R^1$, $R^2$, $R^3$, $R^4$, $R^5$, and $R^6$ are methyl, ethyl, propyl or isopropyl.

The crystallisation can be accomplished when a solution of cabergoline in a suitable solvent, e.g., o-xylene, m-xylene, p-xylene, 1,2,4-trimethylbenzene, n-propylbenzene, ethylbenzene, or iso-propylbenzene is prepared at higher temperature and the concentrated solution is cooled. Another way how to prepare cabergoline solvates with alkyl-aromates is the addition of a suitable aromatic solvent to a concentrated solution of cabergoline in a solvent in which cabergoline is well soluble. Such solvent can be from a group of aliphatic ethers, ketones and esters, like diethylether, acetone and ethyl acetate, or their mixture. The solution can be brought to crystallisation, e.g., by cooling. The solution can be brought to crystallisation alternatively by partial evaporation of the solvent. The solution of cabergoline can be brought to crystallisation also by addition of a solvent in which the particular cabergoline solvate is insoluble, like aliphatic hydrocarbons e.g. petrolether, hexane or heptane or like. Also any combination of the above mentioned techniques or a mixture of solvents can be used to bring the solution of cabergoline to crystallisation of desired solvate.

The crystallisation of cabergoline from alkyl-aromates is also an excellent process for purification of cabergoline prepared by chemical synthesis.

The new cabergoline solvates can be used for preparing of unsolvated forms of cabergoline. These unsolvated forms of cabergoline are cabergoline Forms I, II, and VII. Formation of unsolvated cabergoline forms can be achieved by desolvation under reduced pressure. Advantageously, desolvation under reduced pressure is carried out at higher temperature. Suitable temperature for desolvation lies below the melting point of the cabergoline solvate. Advantageously, the temperature used for desolvation is in the range 40° C.-60° C.

Desolvation of cabergoline solvates can be achieved also by recrystallisation facilitated by stirring of a suspension of a cabergoline solvate in a solvent, which does not form cabergoline solvate or a mixture of such solvents. Advantageously solubility of cabergoline in such mixture is modified by the ratio of solvent, in which is cabergoline soluble, and a solvent, in which cabergoline is insoluble. Example of solvents, in which cabergoline is soluble are aliphatic ethers, ketones or esters of carboxylic acids. Example of solvents, in which cabergoline is insoluble are aliphatic hydrocarbons. The formation of the desired unsolvated cabergoline form can be modified by the temperature, determining the range of thermodynamic stability of the unsolvated form. For example desolvation of solvates at higher temperatures affords preferably cabergoline Form II. Advantageously, the formation of an unsolvated form of cabergoline can be also affected by seeding. Cabergoline Forms I, II, or VII can be used for effective seeding in order to facilitate recrystallisation of solvates to cabergoline Forms I, II, or VII, respectively. The formation of the desired cabergoline form can thus be directed by a suitable temperature and/or seeding control.

Figure 3:
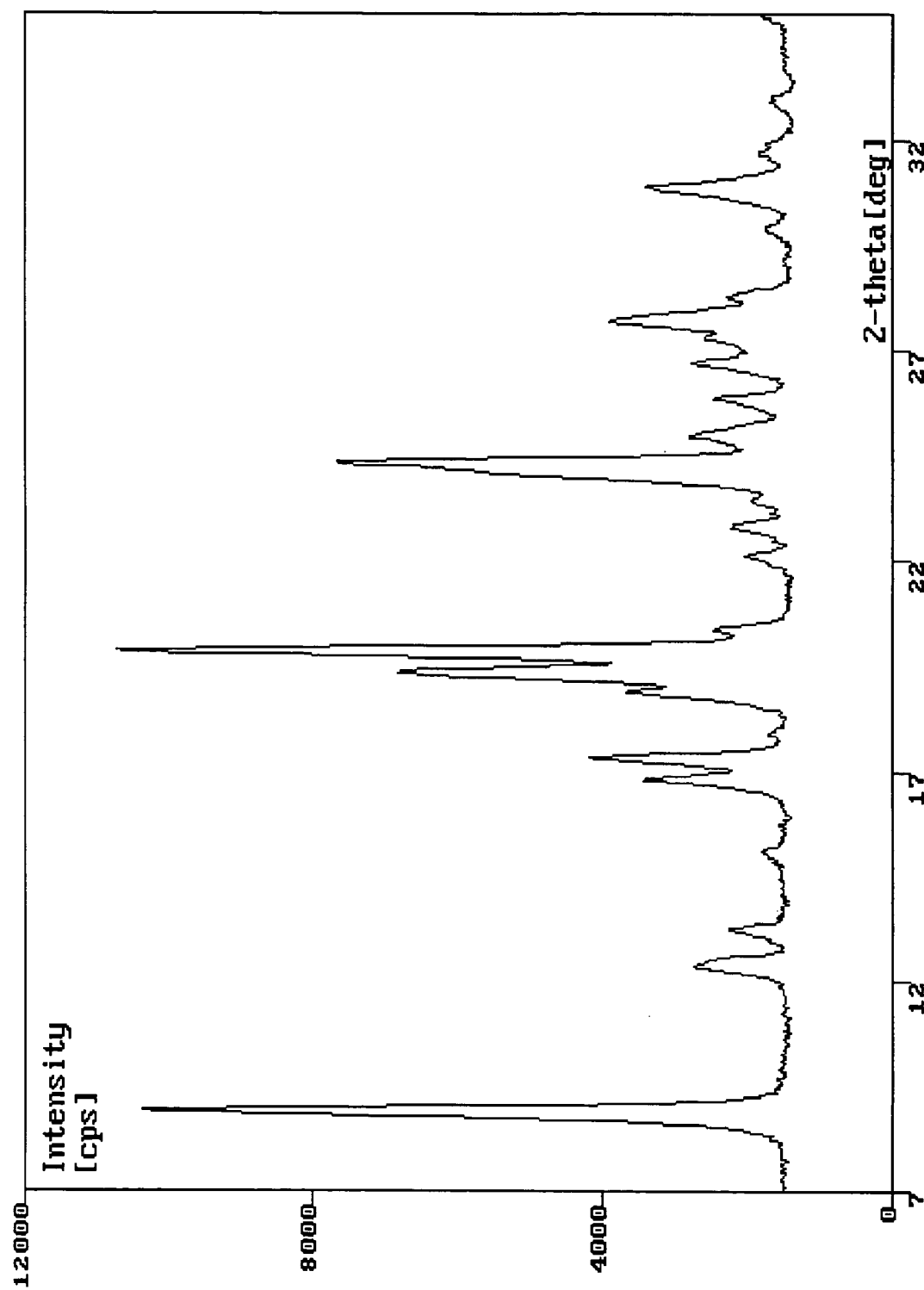
FIG. 3 represents powder diffraction pattern of cabergoline p-xylene solvate Form XI using CoKα radiation.
Figure 11:
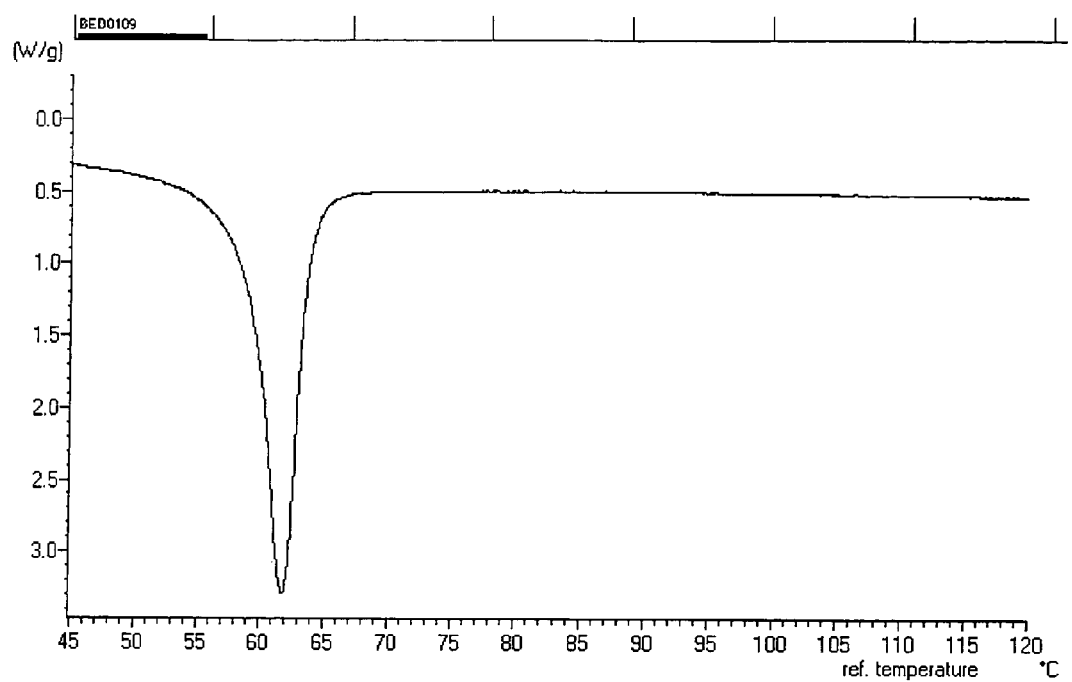
FIG. 11 represents DSC curve of cabergoline Form XI measured on Mettler Toledo DSC 12E thermal analysis system.

In another aspect, the present invention provides a new crystalline form of cabergoline, designated Form XI. Cabergoline Form XI is characterised by a powder X-ray diffraction pattern (FIG. 3) with peaks at about as described in Table 3 (±0.2 degrees two-theta) using a XRD 3000P diffractometer Seifert with CoKα radiation, λ=1.79027 Å, at laboratory temperature, and chemical composition cabergoline:p-xylene approximately 1:1. The DSC record measured on Mettler Toledo DSC 12E thermal analysis system shows the melting of the solvate at about 63° C. as demonstrated on FIG. 11. Cabergoline Form XI differs from all previously described forms of cabergoline by the summary composition $C_{34}H_{47}N_5O_2$ and molecular weight 557.8. However, both the summary composition and molecular weight can correspond to other solvates of cabergoline with xylenes described in this patent from which it can be distinguished by a combination of X-ray diffraction pattern and GC analysis of the solvent molecules.

Table III: X-ray powder diffraction data of cabergoline Form XI using CoKα radiation.

TABLE III

| | angle | D | I rel |
|---|---|---|---|
| 1. | 8.921 | 11.5106 | 953.6 |
| 2. | 12.344 | 8.3259 | 134.1 |
| 3. | 16.800 | 6.1277 | 207.2 |
| 4. | 17.321 | 5.9445 | 287.4 |
| 5. | 18.877 | 5.4587 | 235.3 |
| 6. | 19.336 | 5.3302 | 578.6 |
| 7. | 19.855 | 5.1921 | 1000.0 |
| 8. | 20.357 | 5.0654 | 107.0 |
| 9. | 24.102 | 4.2875 | 448.4 |
| 10. | 24.335 | 4.2470 | 662.8 |
| 11. | 24.953 | 4.1435 | 133.9 |
| 12. | 25.858 | 4.0008 | 96.5 |
| 13. | 26.699 | 3.8770 | 131.1 |
| 14. | 27.297 | 3.7935 | 114.7 |
| 15. | 27.684 | 3.7415 | 256.2 |
| 16. | 30.894 | 3.3608 | 215.0 |

In another aspect, the present invention provides a process for preparing cabergoline Form XI comprising the steps of preparing a solution of cabergoline in a solvent mixture containing p-xylene, cooling the solution below −10° C., adding seeds of cabergoline Form I or XI in order to precipitate cabergoline Form XI and separating cabergoline Form XI.

It was found out that cabergoline crystallises at low temperature from a mixture containing xylenes as a crystalline solvate. The crystallisation can be accomplished when a solution of cabergoline in a suitable amount of the mixture containing xylenes is prepared at higher temperature and the solution is cooled down below −10° C. and then the solution is seeded with crystals of the Form I. The crystalline product formed by further holding of the mixture at the temperature lower than −10° C. can be easily separated by filtration and dried under laboratory temperature in vacuum. It was found out that the crystalline product obtained is a stable xylene solvate and this crystalline product was denominated as Form XI. When the crystallisation was accomplished at the temperature higher than −10° C., the crystalline product obtained was not a pure Form XI but a mixture of the Forms XI and II and other solvated forms of cabergoline.

The crystallisation of the solvate Form XI can be successfully accomplished from a mixture containing xylenes including p-xylene. p-Xylene is also the solvent predominantly incorporated into the crystalline lattice of the solvate, e.g. when the crystallisation was accomplished from the mixture of p- and m-xylenes 2:1 (v/v), the obtained crystalline product contained about 16% of p-xylene and about 2% of m-xylene and when the ratio of both solvents was 1:2, the crystalline product contained about 14% of p-xylene and about 4% of m-xylene. These analytical data clearly indicates that cabergoline Form XI is true solvate of stoichiometry about 1 mole of xylene per 1 mole of cabergoline.

Since p-xylene has relatively high melting point (about 12° C.) its use as a pure xylene is not preferred. The use of p-xylene as a single solvent for obtaining cabergoline Form XI is difficult due to the fact that p-xylene does not enable to perform the crystallisation at required temperature (below −10° C.). When the crystallisation from p-xylene was performed at the temperature above its melting point, cabergoline Form II or a solvate different than the Form XI were obtained. Without any binding to a theory, it was found out by experimentation that suitable mixtures for obtaining of cabergoline Form XI are solvent mixtures containing individual xylenes or mixtures containing them. Preferably, a mixture of p- and m-xylenes can be used. Thus for example, while p-xylene is the solvent affording stable crystalline solvate Form XI, m-xylene with its very low melting point, is the component, which enables to perform the crystallisation at the temperature lower than is the melting point of p-xylene. On the other site, o-xylene affords stable cabergoline solvates and therefore the content of o-xylene in the mixture of xylenes suitable for obtaining the Form XI is restricted. Besides xylenes the mixture of solvents containing xylenes can contain some other solvents, namely ethylbenzene and/or acetone.

In another aspect of the present invention the crystallisation of the Form XI can be accomplished by adding hexane or heptane or another aliphatic hydrocarbon or their mixtures to the crystalline suspension of the Form XI in the crystallisation medium. The crystalline product can be thus obtained in the yield over 98%. The high yield of the crystalline product Form XI, affording finally cabergoline Form I, is the main advantage of the present invention. Another advantage is simplicity of the process. The crystallisation of the cabergoline xylene solvate Form XI can be accomplished within about one hour as documented in Example 9, what is substantially more convenient than the state of the art procedures. Such a simple process can be easily scaled up to the process scale.

Figure 4:
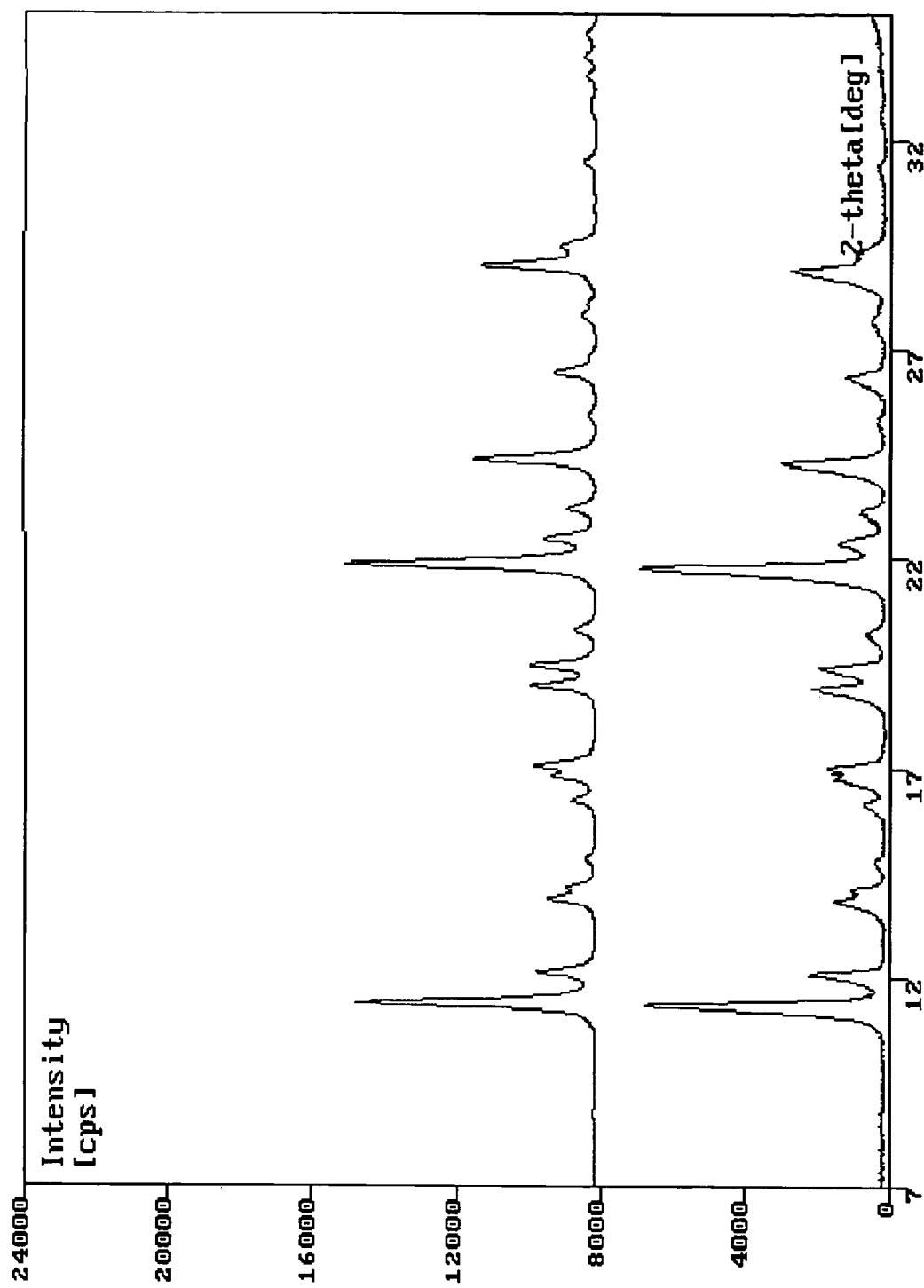
FIG. 4 represents a comparison of characteristic powder diffraction patterns of known cabergoline Form I and cabergoline Form I prepared from cabergoline Form XI. From the top the first curve is calculated powder pattern of cabergoline Form I and the second one is experimental powder diffraction pattern of Form I prepared from cabergoline Form XI using CoKα radiation.
Figure 12:
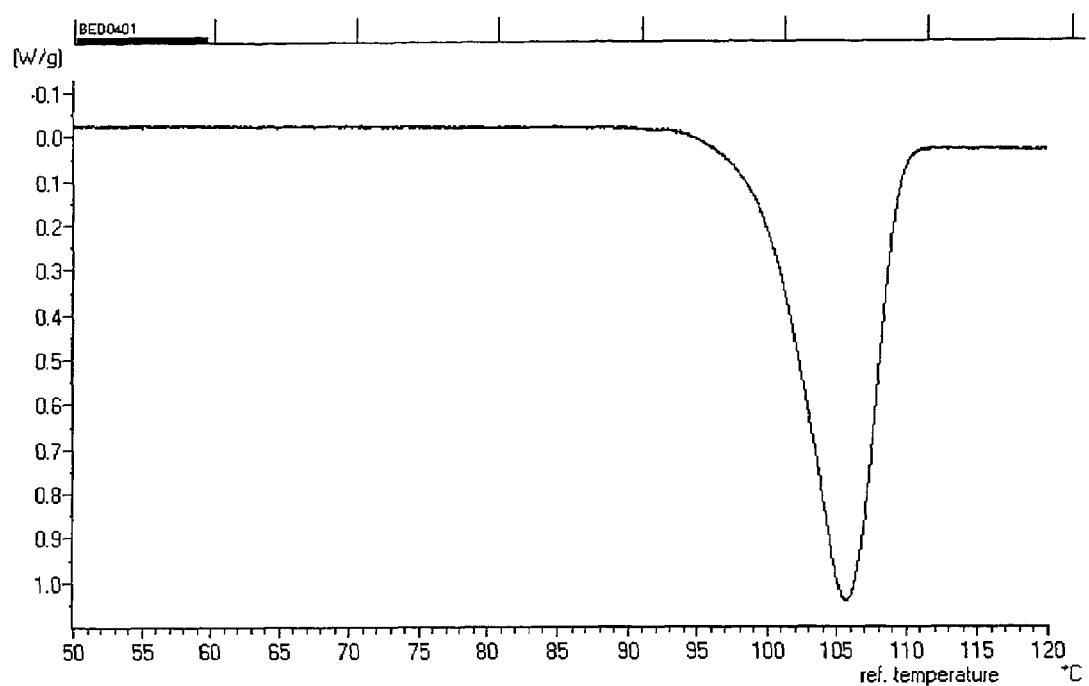
FIG. 12 represents DSC curve of cabergoline Form I measured on Mettler Toledo DSC 12E thermal analysis system.

It was found out by experimentation that the cabergoline xylene solvate Form XI can be transferred to the Form I by drying in high vacuum at the temperature lower than is the melting temperature of the solvate. The desolvation of the xylene solvate Form XI and the transfer of its crystal lattice to the Form I was accomplished at the temperature higher than about 50° C., while long term drying of the solvate at lower temperature (about 45° C.) had no impact on the content of xylenes in the solvate. The change of the crystalline structure of the solvate Form XI during the drying was documented by X-ray powder diffraction pattern (FIG. 4) and the melting point, which corresponds to the known melting point of the Form I (FIG. 12).

The X-ray powder diffraction pattern measurement of the Form I obtained by desolvation of the Form XI was performed using on a XRD 3000P diffractometer Seifert with CoKα radiation, λ=1.79027 Å, at laboratory temperature for 2θ (two theta) values from 7 to 34 providing peaks at about as described in Table 4 (±0.2 degrees two-theta)

Table IV. X-ray powder diffraction data using CoKα radiation of cabergoline Form I prepared from cabergoline form XI.

TABLE IV

|    | angle  | D      | I rel  |
|----|--------|--------|--------|
| 1. | 11.209 | 9.1656 | 849.3  |
| 2. | 11.972 | 8.5833 | 273.5  |
| 3. | 13.676 | 7.5183 | 173.3  |
| 4. | 13.937 | 7.3783 | 116.2  |
| 5. | 16.016 | 6.4256 | 76.3   |
| 6. | 16.717 | 6.1579 | 255.9  |
| 7. | 16.888 | 6.0961 | 232.5  |
| 8. | 18.801 | 5.4804 | 292.4  |
| 9. | 19.262 | 5.3506 | 301.1  |
| 10.| 21.650 | 4.7662 | 1000.0 |
| 11.| 22.277 | 4.6338 | 170.7  |
| 12.| 24.151 | 4.2788 | 459.5  |
| 13.| 26.249 | 3.9422 | 150.0  |
| 14.| 28.746 | 3.6061 | 404.7  |
| 15.| 29.149 | 3.5573 | 116.2  |

Desolvation of cabergoline xylene solvate Form XI can be achieved also by recrystallisation facilitated by stirring of a suspension of the cabergoline solvate Form XI in aliphatic hydrocarbons or a mixture of aliphatic hydrocarbons and xylenes at low temperature. The low temperature of such desolvation is critical because it was found out by experimentation, that other unsolvated forms of cabergoline, e.g. Form II or VII were obtained when the solvent facilitated desolvation was accomplished at higher temperature: while the mixing of the Form XI in hexane at laboratory temperature afforded mainly Form II, mixing at the temperature about 30° C. afforded Form VII. The transformation of the xylene solvate Form XI to Form I was achieved by mixing of the solvate in hexane or a mixture of aliphatic hydrocarbons at the temperature lower than about 0° C. and subsequent slow increase of the temperature up to ambient temperature. Such a low temperature transformation of the Form XI to Form I can be speed up when a low concentration of an aromatic hydrocarbon e.g., a xylene is added to the aliphatic hydrocarbons.

In another aspect of the invention, the Form I of cabergoline can be obtained directly, when an excess of an aliphatic hydrocarbon is added to the crystalline suspension of the Form XI obtained by crystallisation from a mixture of xylenes as described above. Practicing of such attitude is described in Example 12.

Figure 5:
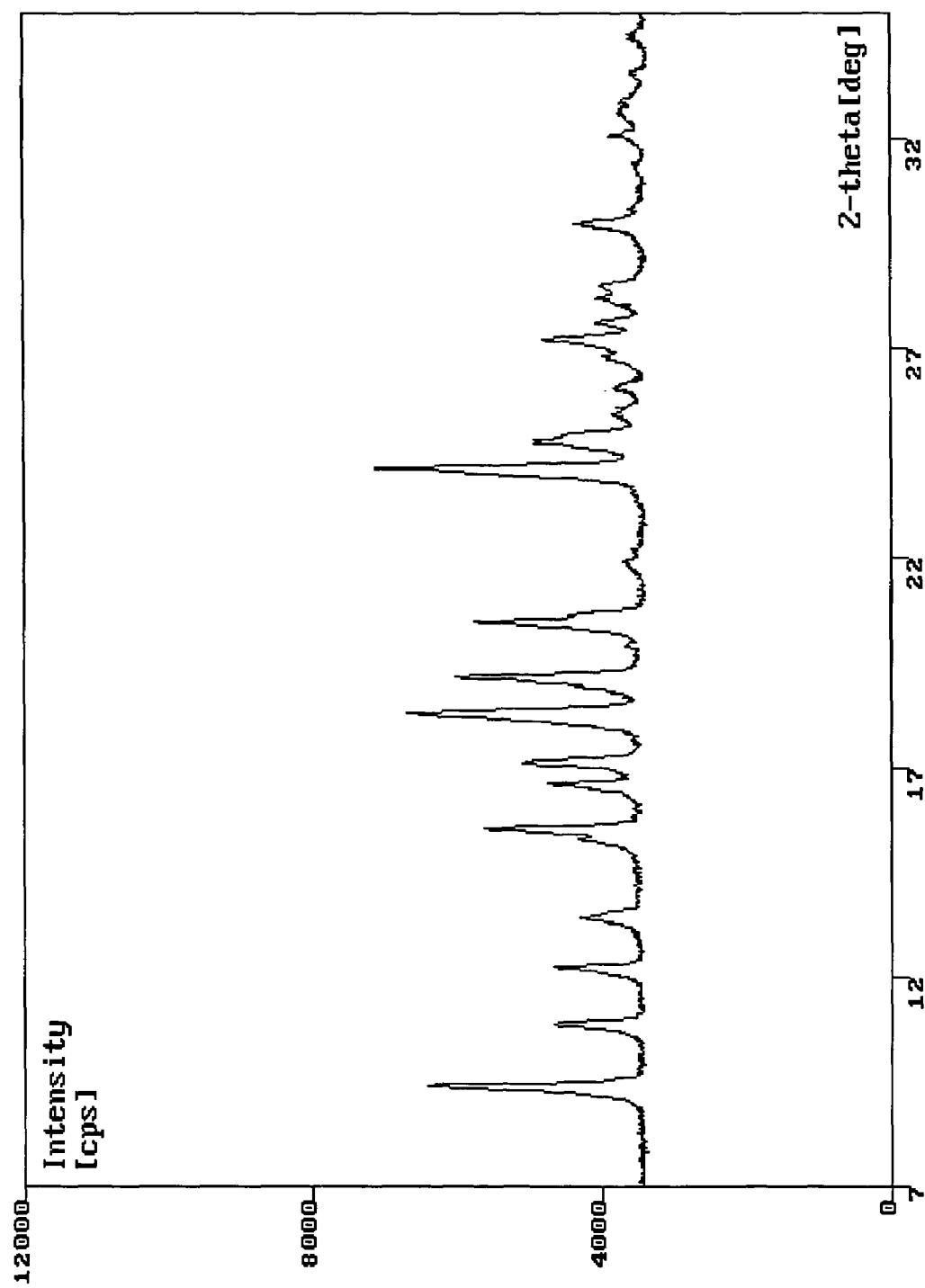
FIG. 5 represents powder diffraction pattern of cabergoline o-xylene solvate Form XII using CoKα radiation.

In another aspect, the present invention provides a new crystalline form of cabergoline, designated Form XII. Cabergoline Form XII is characterised by a powder X-ray diffraction pattern (FIG. 5) with peaks at about as described in Table 5 (±0.2 degrees two-theta) using a XRD 3000P diffractometer Seifert with CoKα radiation, λ=1.79027 Å, at laboratory temperature, and chemical composition cabergoline:o-xylene approximately 1:1. Thus the cabergoline Form XII differs from all previously described forms of cabergoline by the summary composition $C_{34}H_{47}N_5O_3$ and molecular weight 557.8. However, both the summary composition and molecular weight can correspond to other solvates of cabergoline with xylenes described in this patent from which it can be distinguished by a combination of X-ray diffraction pattern and GC analysis of the solvent molecules.

In another aspect, the present invention provides a process for preparing Form XII comprising the steps of preparing a solution of cabergoline in o-xylene or a solvent mixture containing it, cooling the solution to about −10° C. in order to precipitate cabergoline Form XII and separating cabergoline Form XII.

Table 5: X-ray powder diffraction data of cabergoline Form XII using CoKα radiation.

TABLE V

|     | angle  | D       | I rel   |
|-----|--------|---------|---------|
| 1.  | 9.395  | 10.9304 | 790.2   |
| 2.  | 10.873 | 9.4481  | 318.5   |
| 3.  | 12.221 | 8.4091  | 315.2   |
| 4.  | 13.411 | 7.6664  | 201.1   |
| 5.  | 15.287 | 6.7299  | 207.4   |
| 6.  | 15.532 | 6.6246  | 550.0   |
| 7.  | 16.596 | 6.2025  | 310.7   |
| 8.  | 17.084 | 6.0265  | 416.8   |
| 9.  | 18.282 | 5.6346  | 839.9   |
| 10. | 19.164 | 5.3777  | 668.5   |
| 11. | 20.469 | 5.0379  | 590.8   |
| 12. | 24.136 | 4.2815  | 1000.0  |
| 13. | 24.794 | 4.1696  | 388.5   |
| 14. | 26.782 | 3.8651  | 123.2   |
| 15. | 27.190 | 3.8082  | 347.1   |
| 16. | 27.604 | 3.7522  | 160.8   |
| 17. | 28.199 | 3.6745  | 159.8   |
| 18. | 28.491 | 3.6376  | 143.4   |
| 19. | 29.958 | 3.4634  | 243.9   |
| 20. | 32.075 | 3.2401  | 119.7   |

Figure 6:
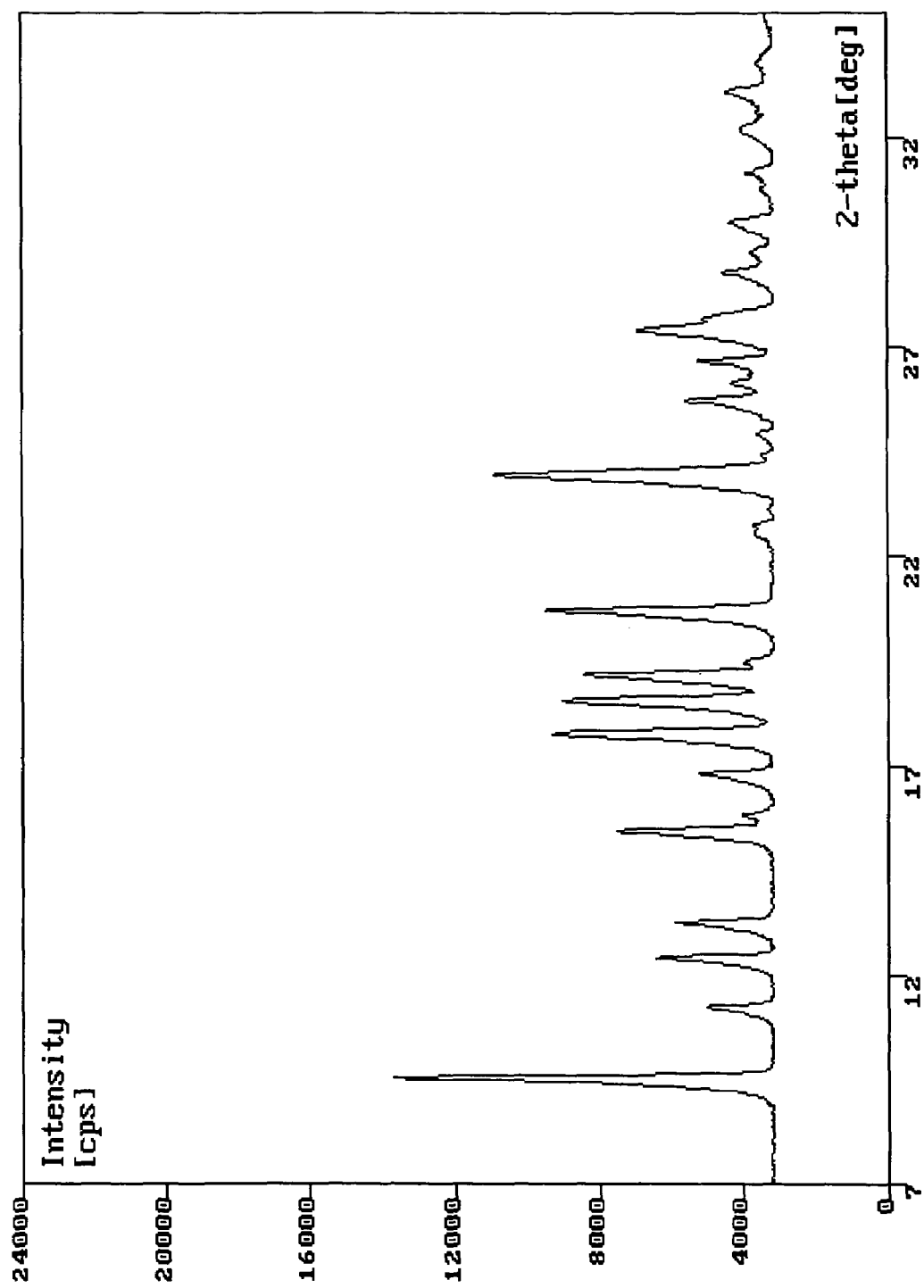
FIG. 6 represents powder diffraction pattern of cabergoline p-xylene solvate Form XVI using CoKα radiation.

In another aspect, the present invention provides a new crystalline form of cabergoline, designated Form XVI. Cabergoline Form XVI is characterised by a powder X-ray diffraction pattern (FIG. 6) with peaks at about as described in Table 6 (±0.2 degrees two-theta) using a XRD 3000P diffractometer Seifert with CoKα radiation, λ=1.79027 Å, at laboratory temperature, and chemical composition cabergoline: p-xylene approximately 1:1. Thus the cabergoline Form XVI differs from all previously described forms of cabergoline by the summary composition $C_{34}H_{47}N_5O_2$ and molecular weight 557.8. However, both the summary composition and molecular weight can correspond to other solvates of cabergoline with xylenes described in this patent from which it can be distinguished by a combination of X-ray diffraction pattern and chemical analysis of solvent molecules.

Cabergoline Form XVI exhibits the following cell parameters symmetry P $2_12_12_1$, a=12.8200(2), b=12.9040(4), c=19.2420(6) Å, V=3183.19(15) Å$^3$ as determined by crystal structure determination on Nonius Kappa CCD area detector, λ(MoK$_α$)=0.71073 Å at 150 K.

Table 6: X-ray powder diffraction data of cabergoline Form XVI using CoKα radiation.

TABLE VI

|    | angle  | D       | I rel  |
|----|--------|---------|--------|
| 1. | 9.541  | 10.7630 | 1000.0 |
| 2. | 11.233 | 9.1460  | 171.4  |
| 3. | 12.417 | 8.2775  | 308.2  |
| 4. | 13.253 | 7.7569  | 253.1  |
| 5. | 15.442 | 6.6628  | 411.7  |
| 6. | 16.811 | 6.1238  | 189.5  |
| 7. | 17.745 | 5.8037  | 582.5  |

TABLE VI-continued

| | angle | D | I rel |
|---|---|---|---|
| 8. | 18.550 | 5.5538 | 550.3 |
| 9. | 19.183 | 5.3724 | 495.8 |
| 10. | 20.707 | 4.9809 | 597.9 |
| 11. | 23.965 | 4.3117 | 734.2 |
| 12. | 25.730 | 4.0204 | 226.9 |
| 13. | 26.143 | 3.9580 | 108.1 |
| 14. | 26.668 | 3.8813 | 191.8 |
| 15. | 27.389 | 3.7810 | 351.7 |
| 16. | 28.782 | 3.6017 | 131.6 |
| 17. | 29.985 | 3.4603 | 109.4 |
| 18. | 33.084 | 3.1440 | 120.1 |

In another aspect, the present invention provides a process for preparing Form XVI comprising the steps of preparing a solution of cabergoline in a solvent mixture containing p-xylene, cooling the solution to about −10° C. in order to precipitate cabergoline Form XVI and separating cabergoline Form XVI.

Figure 7:
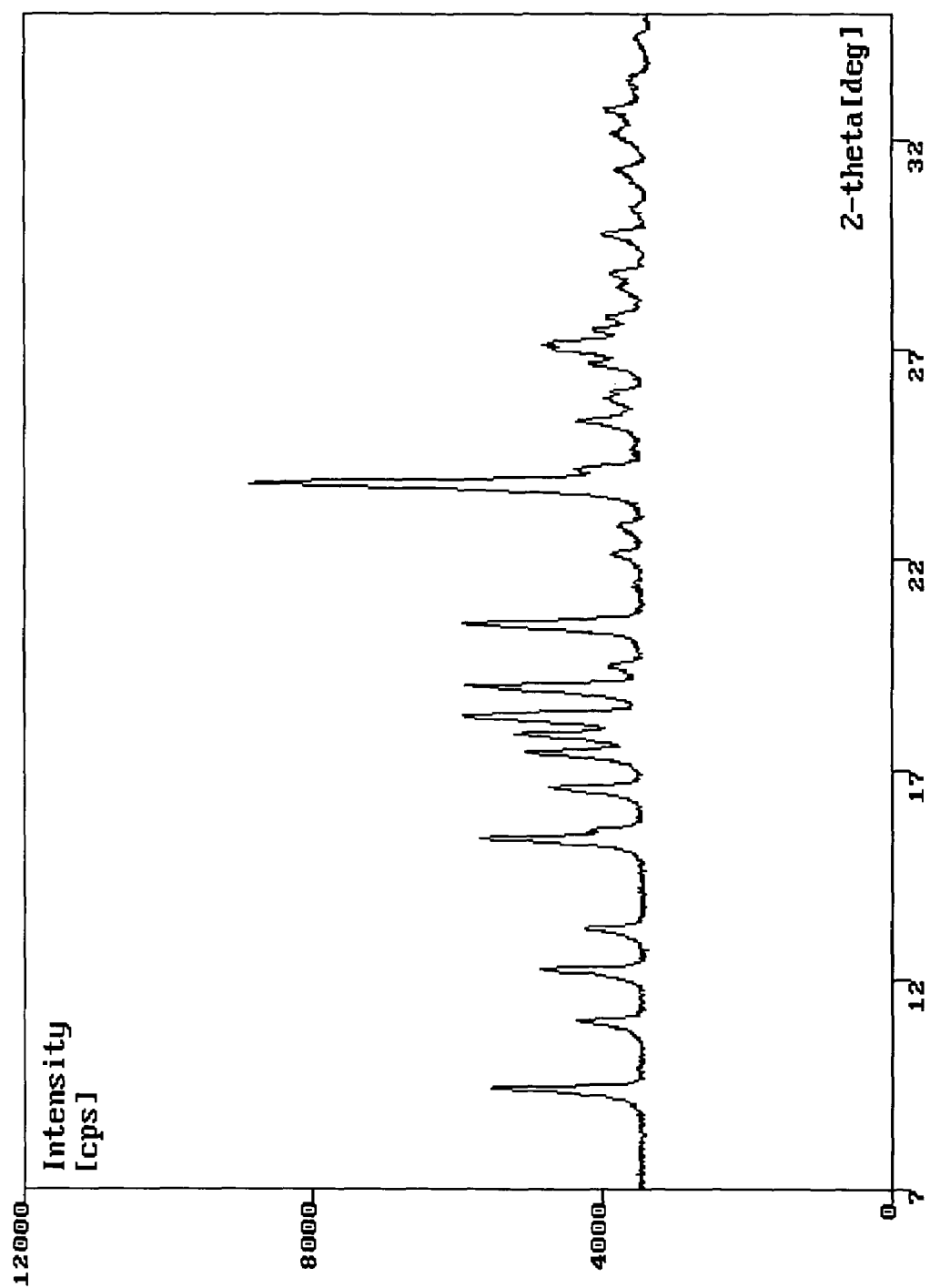
FIG. 7 represents powder diffraction pattern of cabergoline 1,2,4-trimethylbenzene solvate Form XVII using CoKα radiation.

In another aspect, the present invention provides a new crystalline form of cabergoline, designated Form XVII. Cabergoline Form XVII is characterised by a powder X-ray diffraction pattern (FIG. 7) with peaks at about as described in Table 7 (±0.2 degrees two-theta) using a XRD 3000P diffractometer Seifert with CoKα radiation, λ=1.79027 Å, at laboratory temperature, and chemical composition cabergoline:1,2,4-trimethylbenzene approximately 1:1. Thus the cabergoline Form XVII differs from all previously described forms of cabergoline by the summary composition $C_{35}H_{49}N_5O_2$ and molecular weight 571.8. However, both the summary composition and molecular weight can potentially correspond to other solvates of cabergoline with alkyl-aromatic solvents have the general formula $C_6H_5R^1$, where for $R^1$=ethyl, propyl or isopropyl or formula $C_6H_{6-x}R^1_iR^2_jR^3_kR^4_lR^5_mR^6_n$, where x=2, 3, 4, 5, 6, sum of i+j+k+l+m+n=x, and $R^1$, $R^2$, $R^3$, $R^4$, $R^5$, and $R^6$ are methyl, ethyl, propyl or isopropyl, where the solvent has the identical chemical composition as 1,2,4-trimethylbenzene, from which it can be distinguished by a combination of X-ray diffraction pattern and GC analysis of the solvent molecules.

Cabergoline Form XVII exhibits the following cell parameters symmetry P $2_12_12_1$, a=12.9430(2), b=13.0730(4), c=19.1340(5) Å, V=3237.55(14) Å³ as determined by crystal structure determination on Nonius Kappa CCD area detector, λ(MoK$_\alpha$)=0.71073 Å at 150 K.

Table VII: X-ray powder diffraction data of cabergoline Form XVII using CoKα radiation.

TABLE VII

| | angle | D | I rel |
|---|---|---|---|
| 1. | 9.401 | 10.9234 | 384.2 |
| 2. | 12.225 | 8.4064 | 269.3 |
| 3. | 15.348 | 6.7032 | 406.6 |
| 4. | 16.556 | 6.2175 | 219.5 |
| 5. | 17.413 | 5.9137 | 285.7 |
| 6. | 17.847 | 5.7710 | 314.3 |
| 7. | 18.275 | 5.6367 | 452.2 |
| 8. | 18.992 | 5.4259 | 431.0 |
| 9. | 20.471 | 5.0376 | 453.9 |
| 10. | 23.822 | 4.3372 | 1000.0 |
| 11. | 24.152 | 4.2787 | 156.4 |
| 12. | 26.658 | 3.8827 | 111.5 |
| 13. | 27.124 | 3.8174 | 223.8 |
| 14. | 27.480 | 3.7688 | 107.6 |

In another aspect, the present invention provides a process for preparing Form XVII comprising the steps of preparing a solution of cabergoline in 1,2,4-trimethylbenzene or a solvent mixture containing it, cooling the solution to about −10° C. in order to precipitate cabergoline Form XVII and separating cabergoline Form XVII.

Figure 8:
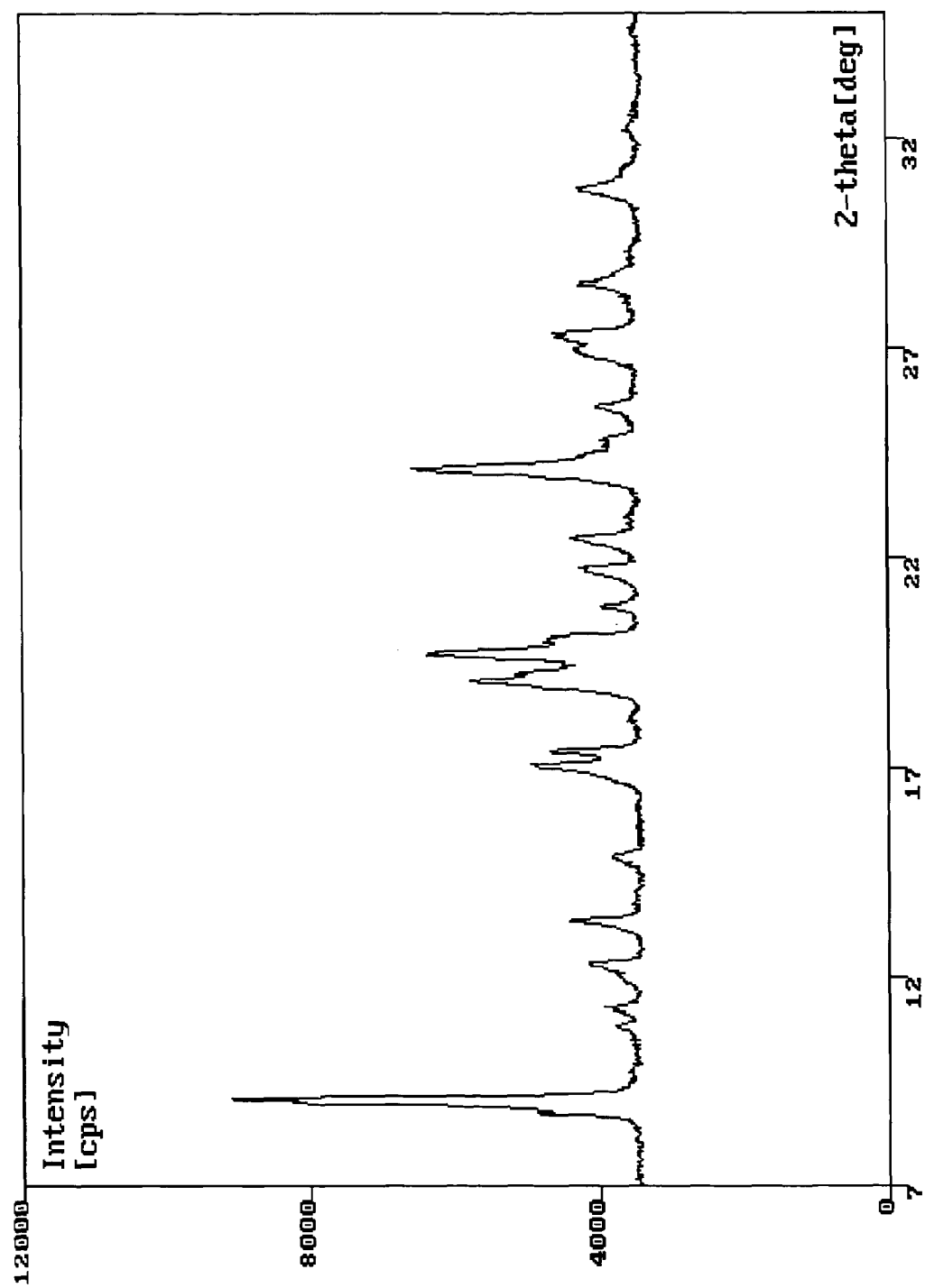
FIG. 8 represents powder diffraction pattern of cabergoline ethylbenzene solvate Form XVIII using CoKα radiation.

In another aspect, the present invention provides a new crystalline form of cabergoline, designated Form XVIII. Cabergoline Form XVIII is characterised by a powder X-ray diffraction pattern (FIG. 8) with peaks at about as described in Table 8 (±0.2 degrees two-theta) using a XRD 3000P diffractometer Seifert with CoKα radiation, λ=1.79027 Å, at laboratory temperature, and chemical composition cabergoline: ethylbenzene approximately 1:1. Thus the cabergoline Form XVIII differs from all previously described forms of cabergoline by the summary composition $C_{35}H_{49}N_5O_2$ and molecular weight 571.8. However, both the summary composition and molecular weight can potentially correspond to other solvates of cabergoline with alkyl-aromatic solvents, e.g. xylenes, or generally with solvents which have the general formula $C_6H_5R^1$, where for $R^1$=ethyl, propyl or isopropyl or formula $C_6H_{6-x}R^1_iR^2_jR^3_kR^4_lR^5_mR^6_n$ where x=2, 3, 4, 5, 6, sum of i+j+k+l+m+n=x, and $R^1$, $R^2$, $R^3$, $R^4$, $R^5$, and $R^6$ are methyl, ethyl propyl or isopropyl, where the solvent has the identical chemical composition as ethylbenzene, from which it can be distinguished by a combination of X-ray diffraction pattern and GC analysis of the solvent molecules.

Table VIII: X-ray powder diffraction data of cabergoline Form XVIII using CoKα radiation.

TABLE VIII

| | angle | D | I rel |
|---|---|---|---|
| 1. | 8.718 | 11.7776 | 238.7 |
| 2. | 9.069 | 11.3221 | 1000.0 |
| 3. | 12.307 | 8.3510 | 120.1 |
| 4. | 13.329 | 7.7132 | 158.6 |
| 5. | 17.045 | 6.0403 | 262.1 |
| 6. | 17.373 | 5.9269 | 217.1 |
| 7. | 19.064 | 5.4057 | 409.7 |
| 8. | 19.230 | 5.3592 | 297.8 |
| 9. | 19.704 | 5.2316 | 524.3 |
| 10. | 20.018 | 5.1505 | 216.2 |
| 11. | 21.766 | 4.7411 | 130.6 |
| 12. | 22.475 | 4.5934 | 156.7 |
| 13. | 24.140 | 4.2809 | 549.3 |
| 14. | 26.984 | 3.8367 | 139.8 |
| 15. | 27.339 | 3.7878 | 188.4 |
| 16. | 28.538 | 3.6319 | 133.3 |
| 17. | 30.786 | 3.3724 | 147.9 |

In another aspect, the present invention provides a process for preparing cabergoline Form XVIII comprising the steps of preparing a solution of cabergoline in ethylbenzene or a solvent mixture containing it, cooling the solution below −10° C., preferably below −25° C., adding seeds of cabergoline Form I in order to precipitate cabergoline Form XVIII and separating cabergoline Form XVIII.

Figure 9:
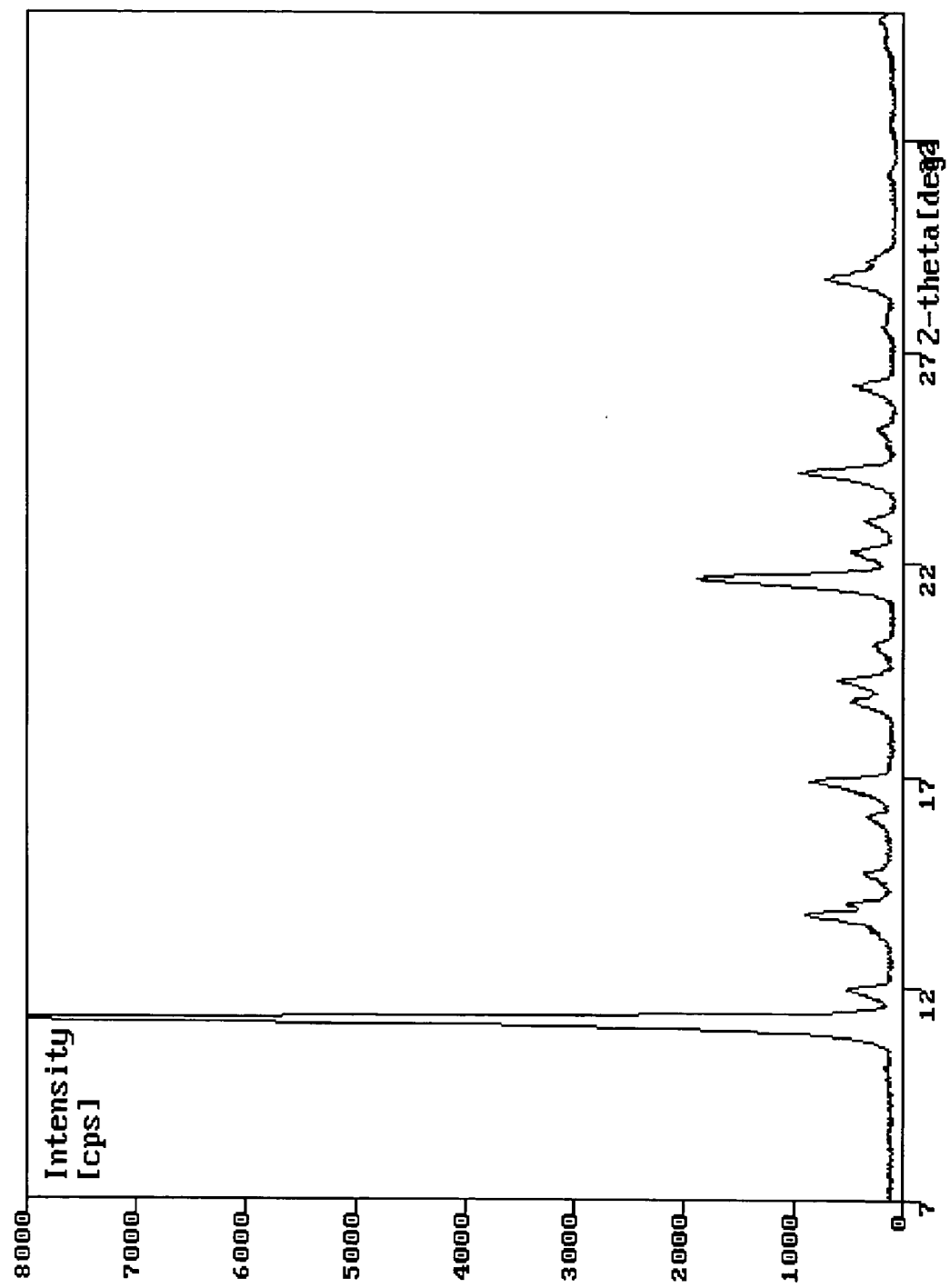
FIG. 9 represents powder diffraction pattern of cabergoline Form I prepared by direct crystallisation from supersaturated solution of cabergoline in toluene using CoKα radiation.

It is still the further embodiment, the new process for direct crystallisation of cabergoline Form I. We disclose here the unexpected effect of super-cooling of concentrated solutions of cabergoline in toluene on the crystallisation of cabergoline Form I. In contrast to previously known processes providing crystallisation of toluene solvates Form V or Form X, which were used as intermediates for the preparation of cabergoline Form I by their desolvation, and in addition the crystallisation of a new cabergoline toluene solvate Form IX described in this patent we disclose here the new process for direct crystallisation of cabergoline Form I. Thus the present invention provides a process for preparing cabergoline Form I comprising the steps of preparing a solution of cabergoline in toluene or a solvent mixture containing it, cooling the solution below −10° C., preferably below −25° C., adding seeds of cabergoline Form I in order to precipitate cabergoline Form I and separating cabergoline Form I. Cabergoline Form I prepared by direct crystallisation from toluene is characterised by a powder X-ray diffraction pattern (FIG. 9) using a XRD 3000P diffractometer Seifert with CoKα radiation, λ=1.79027 Å, at laboratory temperature, and by the absence of a solvent in the crystal lattice.

In another aspect cabergoline solvates can be used directly for the preparation of the dosage forms. The fact that, e.g., tert-butyl methyl ether solvate contains about 16% of tert-butyl methyl ether can not discriminate it, because tert-butyl methyl ether is the solvent of the class III according to the ICH guidelines, where only the daily intake of the residual solvent is limited. Similarly such calculation can be provided also for other solvates, which can be also directly used for the preparation of the dosage forms. Thus, taking into account the low daily dose of cabergoline, e.g., the tert-butyl methyl ether solvate can be used for the manufacture of the dosage forms directly.

Another possibility how the tert-butyl methyl ether solvate or other solvates can be used for the manufacture of the dosage forms containing cabergoline is its use for the manufacture of amorphous cabergoline. In another aspect three different ways for the preparation amorphous cabergoline were found. The first one consists of dissolving cabergoline in a solvent, in which cabergoline is soluble and after evaporation of the solvent, obtaining solid amorphous foam of cabergoline. The solvents suitable for this use are volatile ethers, ketones and esters. Preferred solvent is acetone or its mixture with diethylether. The second process of preparation of amorphous cabergoline consists in dissolving cabergoline in a solvent with the melting point in the range from −80 to +30° C. and freeze drying of the solution obtained. The preferred solvent for this use is tert-butyl alcohol or 1,4-dioxane.

Figure 10:
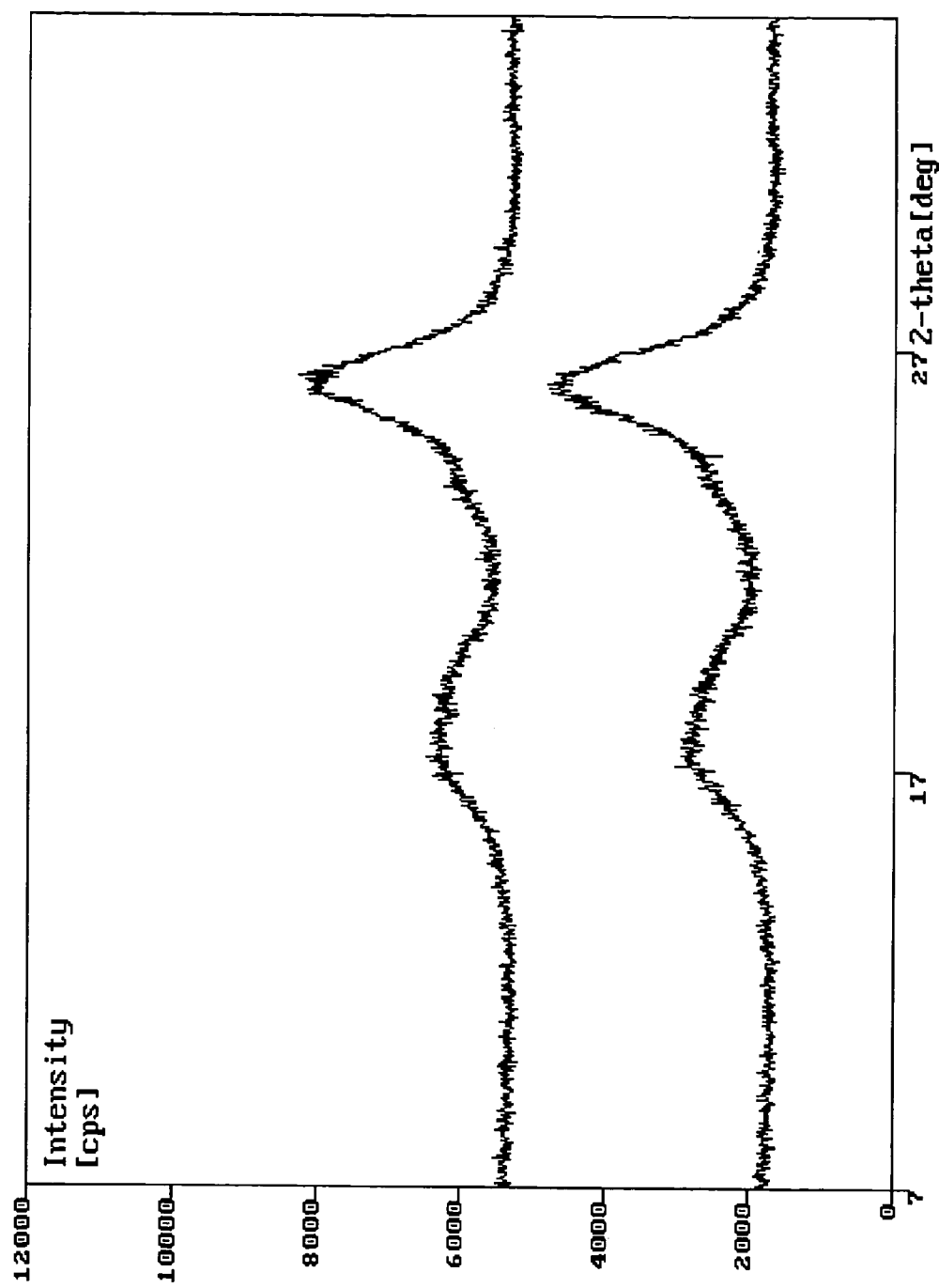
FIG. 10 is a characteristic powder diffraction pattern of amorphous cabergoline on cellulose obtained using CoKα radiation. Top diffractogram represents cellulose triturate containing 5% (w/w) amorphous cabergoline. Bottom diffractogram is cellulose without cabergoline.

The most convenient use of a new cabergoline forms for the manufacture of the dosage form is its transfer to a triturate of amorphous cabergoline with a pharmaceutically acceptable carrier. Such transfer can be accomplished by dissolving of a cabergoline solvate in a solvent in which cabergoline solvate is soluble, addition of a carrier to the solution and evaporation of the solvent from the slurry. The solvents suitable for this process are volatile ethers, ketones and esters. Preferred solution is acetone or its mixture with diethylether, because both of them are solvents of the class III according to ICH limits. The ratio of cabergoline and the carrier is not limited but from the point of view of the stability, the content of cabergoline in the triturate should be less than 10%. The choice of the pharmaceutically acceptable carriers is limited by the fact that the carrier should be insoluble in the used solvent. Therefore the preferred carriers are cellulose, starch, mannitol, lactose or poly(vinylpyrrolidone). The amorphous cabergoline, e.g. on cellulose, is characterised by a powder X-ray diffraction pattern (FIG. 10) using a XRD 3000P diffractometer Seifert with CoKα radiation, λ=1.79027 Å, at laboratory temperature.

EXAMPLES

The following examples further illustrate the present invention, and not meant to limit the scope of the invention.

Example 1

Preparation of Cabergoline Form VIII and Purification of Crude Cabergoline

The foamy evaporation residue (15 g) containing 83.4% of cabergoline according to HPLC analysis, which was obtained from cabergoline synthesis, was dissolved in tert-butyl methyl ether (90 ml) under reflux. The obtained solution was concentrated to a volume of 75 ml, cooled down at approx. 5° C. and let stand at this temperature for 3 hours. The suspension was filtered by means of vacuum using a sintered glass filter. The crystalline solid cake was washed with tert-butyl methyl ether (20 ml) pre-cooled at 5° C. and smoothly dried. Total yield of white cabergoline tert-butyl methyl ether solvate Form VIII of 99.2 purity by HPLC was 12.3 g.

Example 2

Preparation of Cabergoline Form VIII

The foamy evaporation residue containing 20 g of pure cabergoline was dissolved in acetone (40 ml) while heating. After dissolution of the entire cabergoline, tert-butyl methyl ether (200 ml) was added under stirring. The obtained solution was concentrated to a volume of 100 ml, cooled down at approx. 0° C. and let stand at this temperature for 5 hours. The suspension was filtered by means of vacuum using a sintered glass filter. The separated crystalline matter was washed with 30 ml of tert-butyl methyl ether pre-cooled at 0° C. and then smoothly dried. The yield of cabergoline tert-butyl methyl ether solvate Form VIII was about 75% calculated on the weight of starting cabergoline.

Example 3

Preparation of Cabergoline Form XIV

The foamy evaporation residue containing 0.5 g of pure cabergoline was dissolved in diethylether (15 ml). After dissolution of the entire cabergoline, tetrahydropyrane (2 ml) was added under stirring. The crystals formed were filtered by means of vacuum using a sintered glass filter, washed with 3 ml of diethylether, and dried. The yield of cabergoline tetrahydropyrane solvate Form XIV was about 80% calculated on the weight of starting cabergoline.

Example 4

Preparation of Cabergoline Form XV

The foamy evaporation residue containing 0.5 g of pure cabergoline was dissolved in 4 ml of tetrahydrofurane. After dissolution of the entire cabergoline, cyclohexane (200 ml) was added under stirring. The solution was allowed to stand at ambient temperature overnight. Huge crystals formed on the flask walls were collected by filtration and dried. The yield of cabergoline cyclohexane solvate Form XV was about 70% calculated on the weight of starting cabergoline.

Example 5

Preparation of Amorphous Cabergoline by Evaporation

Cabergoline tert-butyl methyl ether solvate Form VIII (26 g) was dissolved in 320 ml of acetone. The prepared solution was evaporated on rotary vacuum evaporator to the state of stabile white foam. The obtained evaporation residue was dried under vacuum at 35° C. until constant weight. Yield of the dried amorphous product was 21.1 g.

Example 6

Preparation of Amorphous Cabergoline by Freeze Drying

Cabergoline tert-butyl methyl ether solvate Form VIII (1.2 g) was dissolved in tert-butyl alcohol (15 ml). The prepared solution was cooled down at approx. −10° C. and let stand at this temperature for 1 hour. The obtained frozen solution was freeze-dried under high vacuum at the ambient temperature for 12 hours. Yield of the amorphous product was 0.95 g.

Example 7

Preparation of Amorphous Cabergoline on a Carrier

Cabergoline tert-butyl methyl ether solvate Form VIII (5.94 g) was dissolved in dry acetone (1200 ml). Microcrystalline cellulose (94.06 g) was added to the prepared cabergoline solution. The resulting heterogeneous mixture was evaporated on rotary vacuum evaporator. The obtained fine white solid was dried under vacuum at 35° C. until constant weight. Yield of the dried amorphous product was 96.4 g.

Example 8

Preparation of Amorphous Cabergoline on a Carrier

Cabergoline tert-butyl methyl ether solvate Form VIII (3.0 g) was dissolved in dry acetone (610 ml). Lactose monohydrate (47.5 g) was added to the prepared cabergoline solution. The resulting heterogeneous mixture was evaporated on rotary vacuum evaporator. The obtained fine white solid was dried under vacuum at 35° C. until constant weight. Yield of the dried product was 42.8 g.

Example 9

Preparation of xylene Solvate Form XI tert-Butyl methyl ether solvate of cabergoline, Form VIII (20.0 g) was dissolved in the mixture of 40 ml p-xylene and 40 ml m-xylene and the solution was cooled to the temperature −25° C. under stirring. Then the solution was seeded with cabergoline Form I (50 mg) and the mixture was stirred for 15 minutes while the temperature was hold in the range from −22 to −25° C. During this time crystalline slurry was obtained. Then 160 ml of n-heptane was dropped into the suspension within 30 minutes under cooling (−22 to −30° C.) and the suspension was filtered and the separated crystalline product was dried at ambient temperature in vacuum (1 mbar) for 24 hours. 20.6 g of xylene solvate Form XI was obtained. According to GC analysis, the product contained 14.97% of p-xylene and 2.49% of m-xylene. The mother liquors after crystallisation of the Form XI were evaporated to dryness giving 0.2 g of dry residue.

Example 10

Desolvation of Cabergoline Xylene Solvate Form XI by Drying

Cabergoline xylene solvate Form XI (5.0 g) prepared in Example 9 was dried in vacuum 1 mbar for 8 hours at 30° C., additional 8 hours at 40° C., 8 hours at 50° C. and finely for 24 hours at 59° C. The dried product was Form I as documented by X-ray diffraction pattern.

Example 11

Desolvation of Cabergoline xylene Solvate Form XI in Hexane

Cabergoline xylene solvate Form XI (5.0 g) prepared in Example 9 was suspended in 25 ml hexane cooled to −20° C. The suspension was stirred for 24 while the temperature was gradually increased up to 25° C. Then the suspension was filtered and the crystalline product was dried for 8 hours in vacuum (1 mbar) at 30° C. The dried product was Form I as documented by X-ray diffraction pattern.

Example 12

Direct Preparation of Cabergoline Form I tert-Butyl methyl ether solvate of cabergoline Form VIII (5.0 g) was dissolved in the mixture of 10 ml p-xylene and 10 ml m-xylene and the solution was cooled to the temperature −25° C. under stirring. Then the solution was seeded with 20 mg of cabergoline Form I and the mixture was stirred for 15 minutes while the temperature was hold in the range from −20 to −26° C. During this time crystalline slurry was obtained. Then 100 ml of n-hexane was dropped into the suspension within 60 minutes under cooling (−20 to −32° C.). The suspension was further stirred for 24 hours while the temperature of the suspension was gradually increased up to 25° C. Then the crystalline product was filtered off, washed with 20 ml of n-hexane and dried in vacuum for 8 hours at 30° C. The dried product was Form I as documented by X-ray diffraction pattern.

Example 13

Preparation of o-xylene Solvate Form XII tert-Butyl methyl ether solvate of cabergoline Form VIII (6.0 g) was dissolved in diethylether (60 ml) and o-xylene (10 ml) was added. Diethylether was evaporated on vacuum evaporator and the solution was cooled to the temperature −15° C. overnight. The crystals were separated by filtration, washed with petrolether/o-xylene mixture (1:1, v/v), than with petrolether and dried on air. The yield of cabergoline o-xylene solvate Form XII was about 60% calculated on the weight of starting cabergoline.

Example 14

Preparation of p-xylene Solvate Form XVI tert-Butyl methyl ether solvate of cabergoline Form VIII (7.0 g) was dissolved in p-xylene (10 ml) and m-xylene (10 ml) under heating to about 60° C. and the solution was cooled to the temperature −10° C. overnight. The crystals were formed spontaneously, separated by filtration, washed with petrolether/p-xylene mixture (1:1, v/v), than with petrolether and dried on air. The yield of cabergoline p-xylene solvate Form XVI was about 60% calculated on the weight of starting cabergoline.

Example 15

Preparation of 1,2,4-trimetylbenzene Solvate Form XVII tert-Butyl methyl ether solvate of cabergoline Form VIII (5.0 g) was dissolved in 1,2,4-trimethylbenzene (10 ml) under heating to about 60° C. and the solution was cooled to the temperature −10° C. overnight The crystals were formed spontaneously, separated by filtration, washed with petrolether/1,2,4-trimethylbenzene mixture (1:1, v/v), than with petrolether and dried on air. The yield of cabergoline 1,2,4-trimethylbenzene solvate Form XVII was about 60% calculated on the weight of starting cabergoline.

Example 16

Preparation of Ethylbenzene Solvate Form XVIII tert-Butyl methyl ether solvate of cabergoline Form VIII (2.0 g) was dissolved in ethylbenzene (6 ml) under heating to about 60° C. and the solution was cooled to the temperature −30° C. Then the solution was seeded with cabergoline Form I (50 mg) The crystals were formed overnight, separated by filtration, washed with petrolether/ethylbenzene mixture (1:1, v/v), than with petrolether and dried on air. The yield of cabergoline ethylbenzene solvate Form XVIII was about 60% calculated on the weight of starting cabergoline.

Example 17

Preparation of Cabergoline Form I b Direct Crystallisation from Toluene tert-Butyl methyl ether solvate of cabergoline Form VIII (5.0 g) was dissolved in toluene (20 ml) under heating to about 60° C. and the solution was cooled to the temperature −30° C. Then the solution was seeded with cabergoline Form I (50 mg) The crystals were formed overnight. Crystals were filtered washed with petrolether and dried on air. The dried product was Form I as documented by X-ray diffraction pattern. The yield of cabergoline Form I was about 50% calculated on the weight of starting cabergoline.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A crystalline cabergoline solvate wherein the solvent in the solvate is selected from the group consisting of cyclohexane, cyclic ethers, alkyl-aromatic solvents of formula $C_6H_5R^1$, wherein $R^1$ is selected from propyl or isopropyl, and alkyl-aromatic solvents of formula $C_6H_6$ wherein at least two hydrogens are substituted by a group selected from the group consisting of methyl, ethyl, propyl and isopropyl.

2. The crystalline cabergoline solvate of claim 1 which is a tetrahydropyran solvate.

3. The crystalline cabergoline solvate of claim 1 which is an cyclohexane solvate.

4. The crystalline cabergoline solvate of claim 1 which is a, p-xylene solvate, m-xylene solvate or o-xylene solvate.

5. The crystalline cabergoline solvate of claim 4 which is a o-xylene solvate.

6. The crystalline cabergoline solvate of claim 1 which is a 1,2,4-trimethyl benzene solvate.

7. A process for preparing the cabergoline solvate of claim 1 comprising the steps of dissolving cabergoline in a solvent and crystallizing the cabergoline solvate from the obtained solution by cooling, by partially evaporating the solvent, by adding a solvent in which the cabergoline solvate is insoluble or by a combination thereof, and recovering the cabergoline solvate from the suspension.

8. A process for preparing the tetrahydropyran cabergoline solvate of claim 2 or the cyclohexane cabergoline solvate of claim 3 comprising the steps of dissolving cabergoline in linear, branched or cyclic ethers, adding a solvent in which cabergoline solvate is insoluble, and adding seeds of a cabergoline solvate selected from the group consisting of tetrahydropyran and cyclohexane.

9. The process for preparing cabergoline solvate of claim 8, wherein the cyclic ether is tetrahydropyran.

10. The process of claim 8, wherein the solvent, in which the cabergoline solvate is insoluble, is selected from the group consisting of aliphatic cyclic hydrocarbons and mixtures thereof.

11. The process of claim 10, wherein the solvent, in which the cabergoline solvate is insoluble, is cyclohexane, hexane or heptane.

12. A process for preparing a cabergoline solvate of claim 1 comprising the steps of dissolving cabergoline in a solvent, in which cabergoline is soluble, and adding a solvent in which cabergoline solvate is insoluble.

13. The process of claim 12, wherein the solvent, in which cabergoline is soluble, is selected from the group consisting of linear, branched or cyclic ketones, esters or ethers and mixtures thereof.

14. A process for purification of cabergoline comprising crystallizing crude cabergoline prepared by chemical synthesis using the cabergoline solvate of claim 1.

15. A process for preparing a cabergoline p-xylene solvate of claim 4 comprising the steps of preparing a solution of cabergoline in a solvent mixture containing p-xylene, cooling the solution below −10° C., adding seeds of cabergoline Form I or XI, and precipitating the cabergoline p-xylene solvate.

16. The process of claim 15, wherein one weight part of the starting cabergoline is dissolved in 2-8 weight parts of the solvent mixture containing p-xylene.

17. The process of claim 15, wherein the solvent mixture containing p-xylene includes no less than 25% and not more than 70% of p-xylene and not more than 10% of o-xylene.

18. The process of claim 17, wherein the other components of the solvent mixture containing p-xylene is m-xylene.

19. The process of claim 15, wherein an aliphatic hydrocarbon is added to the crystalline suspension before separation of the cabergoline p-xylene solvate at the temperature lower than −10° C.

20. The process of claim 19, wherein the aliphatic hydrocarbon is pentane, hexane or heptane or a mixture thereof.

21. The process of claim 15, wherein the solution of cabergoline in the solvent mixture containing p-xylene in the initial step is a crystalline or amorphous cabergoline.

22. A process for preparing a cabergoline solvate of claim 5 comprising the steps of preparing a solution of cabergoline in o-xylene or a solvent mixture containing it, cooling the solution to about −10° C. in order to precipitate a cabergoline o-xylene solvate.

23. A process for preparing cabergoline 1,2,4-trimethylbenzene solvate of claim 6 comprising the steps of preparing a solution of cabergoline in 1,2,4-trimethylbenzene or a solvent mixture containing it, cooling the solution to about −10° C. in order to precipitate a cabergoline 1,2,4-trimethylbenzene solvate.

24. A process for desolvation of the cabergoline solvate with alkyl-aromatic solvents of claim 1 comprising the step of removing a solvent under reduced pressure.

25. A process for desolvation of the cabergoline solvate with alkyl-aromatic solvents of claim 1 comprising the step of stirring a suspension of the cabergoline solvate in a solvent in which cabergoline solvate is insoluble.

26. The process of claim 25, wherein the solvent in which cabergoline solvate is insoluble is selected from the group consisting of aliphatic or cyclic hydrocarbons and mixtures thereof.

27. The process of claim 26, wherein the solvent in which cabergoline solvate is insoluble is pentane, hexane or heptane.

28. A process for purification of cabergoline comprising crystallizing the crude amorphous cabergoline using the cabergoline alkyl-aromatic solvate of claim 1.

29. A process for producing crystalline Form I of cabergoline comprising dissolving a cabergoline p-xylene solvate and desolvating the solvate to the crystalline Form I of cabergoline.

30. The process of claim 29, wherein the step of desolvating the solvate comprises drying of the solvate at the temperature lower than 60° C. and high vacuum.

31. The process of claim 29, wherein the step of desolvating the solvate comprises mixing of the solvate in a suspension of an aliphatic hydrocarbon at the temperature lower than 30° C.

32. The process of claim 31, wherein the aliphatic hydrocarbon is selected from the group consisting of pentane, hexane, and heptane and a mixture thereof.

33. A process for preparing amorphous cabergoline comprising the steps of dissolving a cabergoline solvate of claim 1 in a solvent in which the cabergoline is soluble and evaporating the solution to dryness.

34. The process of claim 33, wherein the solvent is selected from the group consisting of volatile ethers, ketones and esters, and mixtures thereof.

35. The process of claim 34, wherein the solvent is acetone or a mixture of acetone and diethylether.

36. A process for preparing amorphous cabergoline comprising the steps of a dissolving a cabergoline solvate of claim 1 in a solvent in which cabergoline is soluble, freezing of the solution to, and evaporating the volatile solvents by freeze drying under reduced pressure.

37. The process of claim 36, wherein the solvent is selected from the group consisting of solvents with the melting point in the range from −80° C. to 30° C., and mixtures thereof.

38. The process of claim 37, wherein the solvent is 1,4-dioxane or tert-butyl alcohol.

39. A process for preparing a triturate of amorphous cabergoline with a carrier comprising the steps of dissolving a cabergoline solvate in a solvent in which cabergoline is soluble and evaporating the solvent under reduced pressure.

40. The process of claim 39, wherein the solvent is selected from the group consisting of volatile ethers, ketones and esters, and mixtures thereof.

41. The process of claim 40, wherein the solvent is acetone or a mixture of acetone with diethylether.

42. The process of claim 39, wherein the carrier is microcrystalline cellulose, starch, mannitol or lactose or mixtures thereof.

43. A pharmaceutical composition comprising a pharmaceutically effective amount of a crystalline cabergoline solvate of claim 1 and a pharmaceutically acceptable excipient.

44. A pharmaceutical composition comprising a pharmaceutically effective amount of the amorphous cabergoline made in accordance with any one of claim 33, 36, and 39 and a pharmaceutically acceptable excipient.

45. A method of treatment of hyperprolactinemia or parkinsonism in a mammal comprising administering of a pharmaceutical composition according to claim 43 to the mammal in need of treatment thereof.

46. A process for direct crystallization of cabergoline Form I, comprising the steps of preparing a solution of cabergoline in toluene or a solvent mixture containing it, cooling the solution below −10° C., adding seeds of cabergoline Form I in order to precipitate cabergoline Form I, and separating cabergoline Form I.

47. The process of claim 46, wherein the solution is cooled below 25° C.

48. The crystalline cabergoline solvate of claim 2 which is a mono tetrahydropyran solvate.

49. The crystalline cabergoline solvate of claim 48 which is a tetrahydropyran solvate Form XIV.

50. The crystalline cabergoline solvate of claim 2 which is a tetrahydropyran solvate having a powder X-ray diffraction pattern with peaks at 9.3, 12.3, 13.8, 16.0, 19.4, 20.0, 21.3, 24.8, 25.1 and 28.1±0.2 degrees two-theta using CoKα radiation determined at ambient temperature or a symmetry P $2_1 2_1 2_1$ and unit cell parameters of about a=12.9, b=14.3 and c=17.7 Angstroms as determined at 150° K.

51. The crystalline cabergoline solvate of claim 3 which is a mono cyclohexane solvate.

52. The crystalline cabergoline solvate of claim 3 which is a cyclohexane solvate Form XV.

53. The crystalline cabergoline solvate of claim 3 which is a cyclohexane solvate having a powder X-ray diffraction pattern with peaks at 9.3, 12.3, 13.8, 16.0, 19.4, 20.0, 21.3, 24.8, 25.1 and 28.1±0.2 degrees two-theta using COKα radiation determined at ambient temperature or a symmetry P $2_1 2_1 2_1$ and unit cell parameters of about a=12.9, b=14.3 and c=17.7 Angstroms as determined at 150° K.

54. The crystalline cabergoline solvate of claim 4 which is a p-xylene solvate.

55. The crystalline cabergoline solvate of claim 4 which is Form XI or XVI.

56. The crystalline cabergoline solvate of claim 55 which is a p-xylene solvate Form XI having a powder X-ray diffraction pattern with peaks at about 8.9, 12.3, 16.8, 17.3, 18.9, 19.3, 19.9, 20.4, 24.1, 24.3, 25.0, 25.9, 26.7, 27.3, 27.7, and 30.9±0.2 degrees two-theta using CoKα radiation at ambient temperature or an endothermic peak at about 63° C.

57. The crystalline cabergoline solvate of claim 55 which is a p-xylene solvate Form XVI having a powder X-ray diffraction pattern with peaks at about 9.5, 11.2, 12.4, 13.3, 15.4, 16.8, 17.7, 18.6, 19.2, 20.7, 24.0, 25.7, 26.1, 26.7, 27.4, 28.8, 30.0, and 33.1±0.2 degrees two-theta using CoKα radiation at ambient temperature or a symmetry P $2_1 2_1 2_1$ and unit cell parameters a=12.8, b=12.9, c=19.2 Å determined at 150 K.

58. The crystalline cabergoline solvate of claim 5 which is a mono o-xylene solvate.

59. The crystalline cabergoline solvate of claim 5 which is a o-xylene solvate Form XII.

60. The crystalline cabergoline solvate of claim 5 which is a o-xylene solvate Form XII having a powder X-ray diffraction pattern with peaks at about 9.4, 10.9, 12.2, 13.4, 15.3, 15.5, 16.6, 17.1, 18.3, 19.2, 20.5, 24.1, 24.8, 26.8, 27.2, 27.6, 28.2, 28.5, 30.0, and 32.1±0.2 degrees two-theta using CoKα radiation determined at ambient temperature.

61. The crystalline cabergoline solvate of claim 6 which is a mono 1,2,4-trimethyl benzene solvate.

62. The crystalline cabergoline solvate of claim 6 which is a 1,2,4-trimethyl benzene solvate Form XVII.

63. The crystalline cabergoline solvate of claim 6 which is a 1,2,4-trimethyl benzene solvate Form XVII having a powder X-ray diffraction pattern with peaks at about 9.4, 12.2, 15.3, 16.6, 17.4, 17.8, 18.3, 19.0, 20.5, 23.8, 24.2, 26.7, 27.1, and 27.5±0.2 degrees two-theta using CoKα radiation determined at ambient temperature or a symmetry P $2_1 2_1 2_1$ and unit cell parameters a=12.9, b=13.1, c=19.1 Å determined at 150 K.

64. The process of claim 15, wherein said precipitated p-xylene solvate is Form XI.

65. The pharmaceutical composition of claim 43 wherein the crystalline cabergoline is selected from the group consisting of Forms XI, XII, XIV, XV and XVI.

66. The process of preparing the tetrahydropyran cabergoline solvate of 2 comprising the steps of dissolving cabergoline in a solvent, and adding a solvent in which cabergoline solvate is insoluble.

67. The process of claim 66, wherein the solvent in which the cabergoline solvate is insoluble is tetrahydropyran.

68. The process of claim 12, wherein the solvent in which the cabergoline solvate is insoluble is cyclohexane.

69. The process of preparing the p-xylene cabergoline solvate of claim 4 comprising the steps of preparing a solution of cabergoline in p-xylene or a solvent mixture containing it, and cooling the solution to about −10° C. in order to precipitate a cabergoline p-xylene solvate.

70. A method of treatment of hyperprolactinemia or parkinsonism in a mammal comprising administering of a pharmaceutical composition according to claim 22 to the mammal in need of treatment thereof.

71. A method of treatment of hyperprolactinemia or parkinsonism in a mammal comprising administering of a pharmaceutical composition according to claim 65 to the mammal in need of treatment thereof.

\* \* \* \* \*

UNITED STATES PATENT AND TRADEMARK OFFICE
CERTIFICATE OF CORRECTION

PATENT NO.         : 7,531,551 B2
APPLICATION NO.    : 10/841813
DATED              : May 12, 2009
INVENTOR(S)        : Roman Bednar et al.

Page 1 of 1

It is certified that error appears in the above-identified patent and that said Letters Patent is hereby corrected as shown below:

Column 19, line 51, "an" should read --a--.

Column 19, line 52, after "a", delete ",".

Column 19, line 54, "a" should read --an--.

Column 20, line 38, "components" should read --component--.

Column 21, line 35, after "steps of", delete "a".

Column 21, line 37, after "solution", delete "to".

Column 21, line 62, "claim" should read --claims--.

Column 21, lines 64-65, "parkinsonism" should read --Parkinsonism--.

Column 22, line 28, "CO" should read --Co--.

Column 22, line 52, "a" should read --an--.

Column 22, line 54, "a" should read --an--.

Column 24, line 8, "22" should read --44--.

Column 24, lines 11-12, "parkinsonism" should read --Parkinsonism--.

Signed and Sealed this

Thirty-first Day of August, 2010

David J. Kappos
*Director of the United States Patent and Trademark Office*